United States Patent
Guzi et al.

(10) Patent No.: US 7,271,175 B2
(45) Date of Patent: Sep. 18, 2007

(54) 17β-HYDROXYSTEROID DEHYDROGENASE TYPE 3 INHIBITORS FOR THE TREATMENT OF ANDROGEN DEPENDENT DISEASES

(75) Inventors: Timothy J. Guzi, Chatham, NJ (US); Yi-Tsung Liu, Morris Township, NJ (US); Ronald J. Doll, Convent Station, NJ (US); Anil Saksena, Upper Montclair, NJ (US); Viyyoor Girijavallabhan, Parsippany, NJ (US); Jonathan A. Pachter, Chatham, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 11/360,711

(22) Filed: Feb. 23, 2006

(65) Prior Publication Data

US 2006/0142338 A1    Jun. 29, 2006

Related U.S. Application Data

(62) Division of application No. 10/735,983, filed on Dec. 15, 2003, now Pat. No. 7,053,091.

(60) Provisional application No. 60/434,101, filed on Dec. 17, 2002.

(51) Int. Cl.
*A61K 31/4375* (2006.01)
*C07D 221/06* (2006.01)

(52) U.S. Cl. ........................... 514/290; 546/79
(58) Field of Classification Search ................ 514/290; 546/79
See application file for complete search history.

(56) References Cited

U.S. PATENT DOCUMENTS

| | | | |
|---|---|---|---|
| 6,162,804 A * | 12/2000 | Bilodeau et al. ......... | 514/234.5 |
| 6,362,188 B1 | 3/2002 | Guzi et al. | |
| 6,541,463 B1 | 4/2003 | Labrie et al. | |

FOREIGN PATENT DOCUMENTS

| | | |
|---|---|---|
| EP | 1122242 | 8/2001 |
| WO | WO86/01105 | 2/1986 |
| WO | WO 86/01105 | 2/1986 |
| WO | WO90/10462 | 9/1990 |
| WO | WO 90/10462 | 9/1990 |
| WO | WO 91/00731 | 1/1991 |
| WO | WO91/00731 | 1/1991 |
| WO | WO 91/00733 | 1/1991 |
| WO | WO91/00733 | 1/1991 |
| WO | WO 94/26767 | 11/1994 |
| WO | WO94/26767 | 11/1994 |
| WO | WO 96/26201 | 8/1996 |
| WO | WO96/26201 | 8/1996 |
| WO | WO 97/11162 | 3/1997 |
| WO | WO97/11162 | 3/1997 |
| WO | WO 99/46279 | 9/1999 |
| WO | WO99/46279 | 9/1999 |
| WO | WO9946279 | 9/1999 |
| WO | WO 03/022835 | 3/2003 |
| WO | WO 03/033487 | 4/2003 |
| WO | WO 2004/046111 | 6/2004 |

OTHER PUBLICATIONS

Tsakovska, et al., "Molecular modeling of triazine type MDR modulators using CoMFA and CoMSIA approaches," SAR and QSAR in Environmental Research, vol. 13, No. 3-4, pp. 487-498 (2002).*
International Search Report of OC06001-01 (7 pgs).

* cited by examiner

*Primary Examiner*—Golam M. M. Shameem
*Assistant Examiner*—Andrew B. Freistein
(74) *Attorney, Agent, or Firm*—Palaiyur S. Kalyanaraman; Serena Farquharson-Torres

(57) ABSTRACT

In its many embodiments, the present invention provides a novel class of compounds as inhibitors of type 3 17β-hydroxysteroid dehydrogenase, methods of preparing such compounds, pharmaceutical compositions containing one or more such compounds, methods of preparing pharmaceutical formulations comprising one or more such compounds, and methods of treatment, prevention, inhibition, or amelioration of one or more diseases associated with type 3 17β-hydroxysteroid dehydrogenase using such compounds or pharmaceutical compositions.

9 Claims, No Drawings

17β-HYDROXYSTEROID DEHYDROGENASE TYPE 3 INHIBITORS FOR THE TREATMENT OF ANDROGEN DEPENDENT DISEASES

FIELD OF THE INVENTION

This application is a divisional of U.S. application Ser. No. 10/735,983, filed Dec. 15, 2003 now U.S. Pat. No. 7,053,091, and claims the benefit of U.S. Provisional Application Ser. No. 60/434,101, filed Dec. 17, 2002.

BACKGROUND OF THE INVENTION

Androgen dependent diseases, for example, diseases whose onset or progress is aided by androgenic activity, are well known. These diseases include, but are not limited to, prostate cancer, benign prostatic hyperplasia, acne, seborrhea, hirsutism, androgenic alopecia, precocious puberty, adrenal hyperlasia and polycystic ovarian syndrome. Estrogen dependent diseases, for example, diseases whose onset or progress is aided by estrogenic activity, are also well known. These include, but are not limited to, breast cancer, endometriosis, leiomyoma and precocious puberty.

Androgenic and estrogenic activities can be suppressed by administering, respectively, androgen and estrogen receptor antagonists. See, for e.g., WO 94/26767 and WO 96/26201. Androgenic and estrogenic activities can also be reduced by suppressing androgen and estrogen biosyntheses using inhibitors of enzymes that catalyze one or more steps of such biosyntheses. 17β-HSD3 is the primary enzyme that converts androstenedione to testosterone in the testes. Inhibitors of both Type 3 and Type 5 17β-hydroxysteroid dehydrogenase are described in WO 99/46279. Inhibitors of Type 5 17β-hydroxysteroid dehydrogenase is also described in WO 97/11162. Androgenic and estrogenic activities can also be reduced by suppressing ovarian or testicular secretions by known methods. See, for e.g., WO 90/10462, WO 91/00731, WO 91/00733 and WO 86/01105.

Commonly owned, pending U.S. patent application Ser. No. 10/235,627, filed Sep. 5, 2002, and Ser. No. 10/271,358, filed Oct. 15, 2002, disclose certain types of inhibitors of type 3 17β-hydroxysteroid dehydrogenase. Pending provisional patent application Ser. No. 60/427,363, filed Nov. 18, 2002, discloses certain types of inhibitors of type 3 17β-hydroxysteroid dehydrogenase too.

There is a continuing need for new compounds, formulations, treatments and therapies to treat diseases and disorders associated with type 3 17β-hydroxysteroid dehydrogenase. It is, therefore, an object of this invention to provide compounds useful in the treatment or prevention or amelioration of such diseases and disorders.

SUMMARY OF THE INVENTION

In its many embodiments, the present invention provides a novel class of compounds as inhibitors of type 3 17β-hydroxysteroid dehydrogenase, methods of preparing such compounds, pharmaceutical compositions comprising one or more such compounds, methods of preparing pharmaceutical compositions comprising one or more such compounds, and methods of treatment, prevention, inhibition or amelioration of one or more diseases associated with type 3 17β-hydroxysteroid dehydrogenase using such compounds or pharmaceutical compositions.

In one aspect, the present application discloses a compound, or a pharmaceutically acceptable salt or solvate of said compound, said compound having the general structure shown in Formula I:

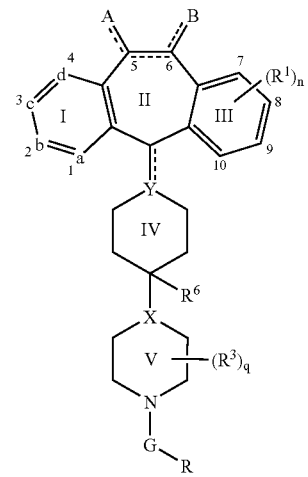

Formula I wherein:

X is CH or N;

Y is selected from the group consisting of C, CH or N, and when Y is CH or N, the optional covalent bond (represented by the dotted line between rings marked II and IV) is absent, and when Y is C, that optional covalent bond is present;

G is $(CHR^4)_n$ or $C(=O)$;

R is selected from the group consisting of alkyl, $-OR^4$, aryl, heteroaryl, heteroaryloxy, heterocyclyl, heterocyclyloxy, cycloalkyl, cycloalklyloxy, $-N(R^4)_2$ where the two $R^4$ moieties can be the same or different, $-(CH_2)_n$-aryl, $-(CH_2)_n$-heteroaryl, $-(CH_2)_n$-heterocyclyl and $-(CH_2)_n$-cycloalkyl, wherein each of said alkyl, aryl, heteroaryl, heterocyclyl and cycloalkyl can be unsubstituted or optionally independently substituted with one or more moieties which can be the same or different, each being independently selected from the group consisting of alkyl, aryl, heteroaryl, $-OR^4$, heterocyclyl, heterocycly-loxy, cycloalkyl, cycloalklyloxy, $-N(R^4)_2$ where the two $R^4$ moieties can be the same or different, $-C(O)R^4$, and $-C(O)N(R^4)_2$ where the two $R^4$ moieties can be the same or different;

one of a, b, c and d represents N or $N^+O^-$, and the remaining a, b, c and d groups represent $C(R^1)$ or $C(R^2)$; or each of a, b, c, and d are independently selected from $C(R^1)$ or $C(R^2)$;

$R^1$ and $R^2$ can be the same or different, each being independently selected from the group consisting of:

H, halo, $-CF_3$, $-OR^4$, $-C(O)R^4$, $-OCF^3$, $-SR^4$, $-S(O)_nR^5$, benzotriazol-1-yloxy, tetrazol-5-ylthio, alkynyl, alkenyl wherein said alkenyl can be unsubstituted or optionally substituted with halo, $-OR^4$ or $-C(O)OR^4$, alkyl wherein said alkyl can be unsubstituted or optionally substituted with halo, $-OR^4$ or $-C(O)OR^4$, $-N(R^4)_2$ where the two $R^4$ moieties can be the same or different, $-NO_2$, $-OC(O)R^5$, $-C(O)OR^4$, $-CN$, $-N(R^4)C(O)OR^4$, —SR⁵C(O)OR⁴, and —SR⁵N(R⁴)₂ (provided that R⁵ in —SR⁵N(R⁴)₂ is not —CH₂—) wherein each R⁴ is independently selected;

the dotted line between carbon atoms 5 and 6 represents an optional bond,
  such that when a double bond between carbon atoms 5 and 6 is present, A and B can be the same or different, each being independently selected from the group consisting of —R⁴, halo, —OR⁴, —C(O)OR⁴, —OC(O)OR⁴ or —OC(O)R⁴, and when no double bond is present between carbon atoms 5 and 6, A and B can be the same or different, each being independently selected from the group consisting of (H₂), —(OR⁵)₂, (H and halo), (dihalo), (H and R⁵), (R⁵)₂, (H and —OC(O)R⁴), (H and —OR⁴), (=O), and (H, (=NOR⁴) or (—O—(CH₂)ₚ—O—) wherein p is 2, 3 or 4);

R³ is selected from the group consisting of H, alkyl, alkoxy and alkoxyalkyl;
R⁴ is selected from the group consisting of H, alkyl, aryl and aralkyl;
R⁵ is alkyl or aryl;
R⁶ is H or alkyl;
n is a number from 1-4; and
q is a number from 1-8.

The compounds of Formula I can be useful as inhibitors of type 3 17β-hydroxysteroid dehydrogenase and can be useful in the treatment and prevention of diseases associated with type 3 17β-hydroxysteroid dehydrogenase.

DETAILED DESCRIPTION

In one embodiment, the present invention discloses compounds which are represented by structural Formula I, or a pharmaceutically acceptable salt or solvate thereof, wherein the various moieties are as described above.

In a preferred embodiment, position a in ring I is N or N⁺O⁻.

In another preferred embodiment, A and B in ring II are H₂, i.e., the optional bond is absent, and the C5-C6 bridge is unsubstituted.

In another preferred embodiment, R¹ and R² can be the same or different, each being independently H or halo.

In another preferred embodiment, R is selected from the group consisting of unsubstituted alkyl, alkyl substituted with a heterocyclyl, —N(R⁴)₂ where the two R⁴ moieties can be the same or different, and —OR⁴, wherein said heterocyclyl can be unsubstituted or optionally substituted with one or more moieties which can be the same or different, each being independently selected from the group consisting of alkyl, aryl, —OR⁴, —N(R⁴)₂ where the two R⁴ moieties can be the same or different, —C(O)R⁴, and —C(O)N(R⁴)₂ where the two R⁴ moieties can be the same or different.

In another preferred embodiment, X is CH.
In another preferred embodiment, X is N.
In another preferred embodiment, Y is N.
In another preferred embodiment, Y is CH.
In another preferred embodiment, R³ is H and q is 8.
In another preferred embodiment, R³ is alkyl and q is 1.
In another preferred embodiment, R³ is alkoxyalkyl and q is 1.
In another preferred embodiment, R³ is aralkyl.
In another preferred embodiment, R⁴ is H, alkyl or aryl.
In another preferred embodiment, R⁵ is alkyl.
In another preferred embodiment, R⁶ is H.
In an additional preferred embodiment, position a in ring I is N.

In an additional preferred embodiment, position a in ring I is N and positions b, c and d are all the same and are C(R¹).

In an additional preferred embodiment, R¹ and R² are the same or different, each being independently selected from H, Br, F and Cl. Non-limiting, illustrative substitutions on rings I and III of formula 1 include trihalo, dihalo and monohalo substituted compounds, such as, for example: (i) 3,8,10-trihalo; (ii) 3,7,8-trihalo; (iii) 3,8-dihalo; (iv) 8-halo; (v) 10-halo; and (vi) 3-halo (i.e., no substituent in Ring III) substituted compounds; wherein each halo is independently selected. Preferred compounds of formula I include: (1) 3-Br-8-Cl-10-Br-substituted compounds; (2) 3-Br-7-Br-8-Cl-substituted compounds; (3) 3-Br-8-Cl-substituted compounds; (4) 3-Cl-8-Cl-substituted compounds; (5) 3-F-8-Cl-substituted compounds; (6) 8-Cl-substituted compounds; (7) 10-Cl-substituted compounds; (8) 3-Cl-substituted compounds; (9) 3-Br-substituted compounds; and (10) 3-F-substituted compounds.

In an additional preferred embodiment, R is selected from the group consisting of unsubstituted alkyl, alkyl substituted with a heterocyclyl, —NH₂, and t-butoxy, wherein said heterocyclyl can be unsubstituted or optionally substituted with one or more moieties selected from the group consisting of —C(O)alkyl, and —C(O)N(alkyl)₂ where the two alkyl moieties can be the same or different.

In an additional preferred embodiment, R³ is tert-butyl and q is 1.

In an additional preferred embodiment, R³ is 2-(methoxy)ethyl and q is 1.

In an additional preferred embodiment, R³ is n-butyl and q is 1.

In an additional preferred embodiment, R³ is benzyl and q is 1.

In an additional preferred embodiment, R⁴ is H.
In an additional preferred embodiment, R⁴ is alkyl.
In an additional preferred embodiment, R⁵ is methyl.
In an additional preferred embodiment, n is 1.
In an additional preferred embodiment, q is 1.
In an additional preferred embodiment, p is 1.

A particularly preferred group of compounds are shown in Table 1.

TABLE 1

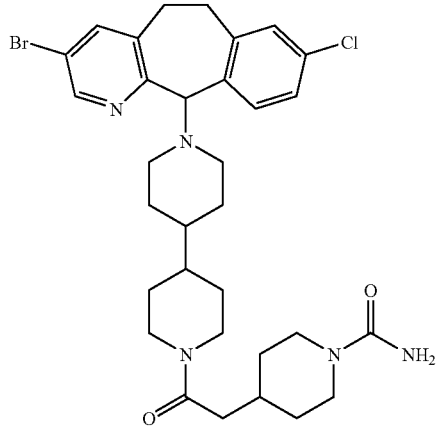

TABLE 1-continued
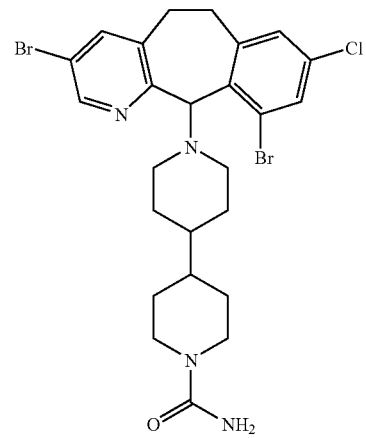
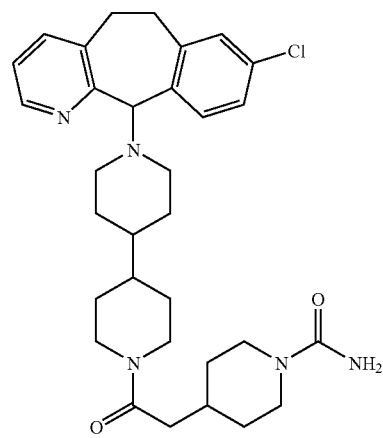
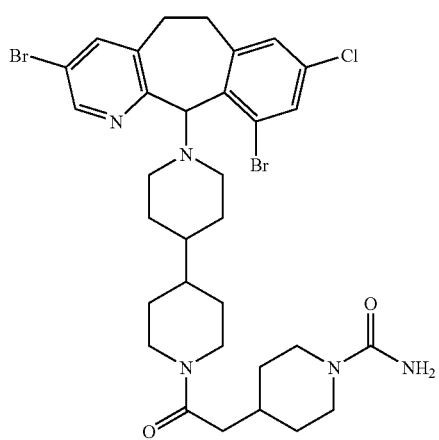
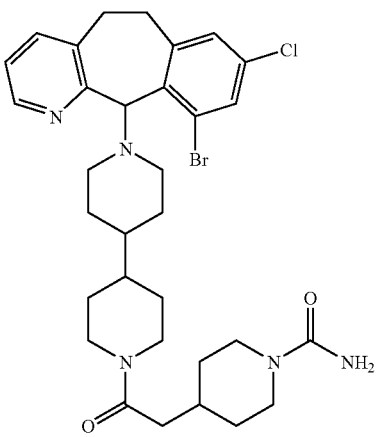
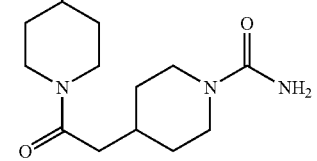

TABLE 1-continued
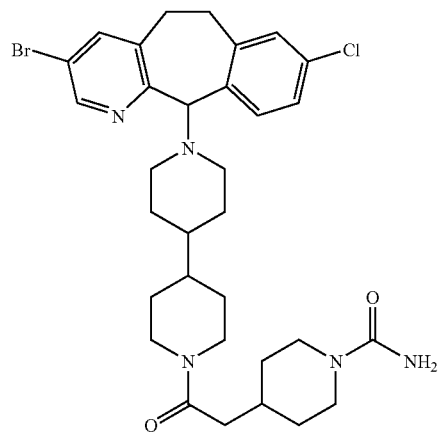
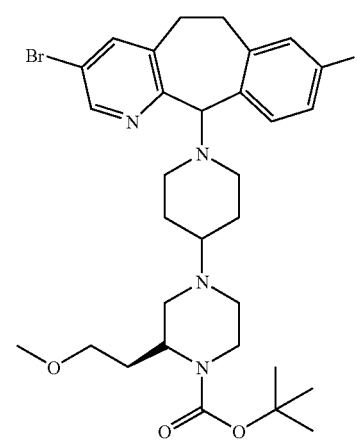
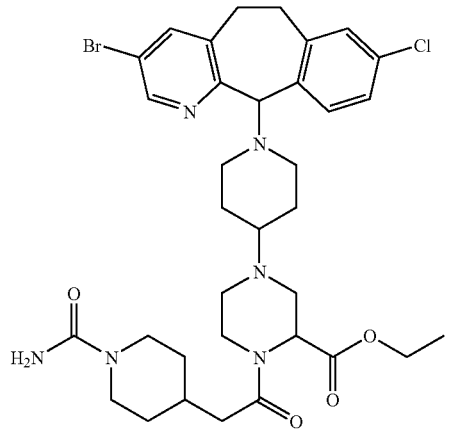
TABLE 1-continued
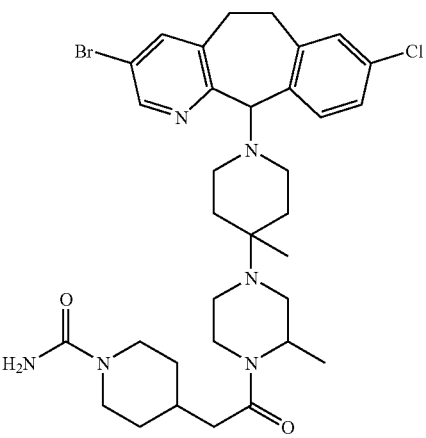
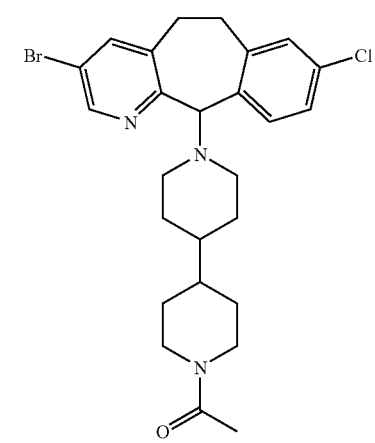
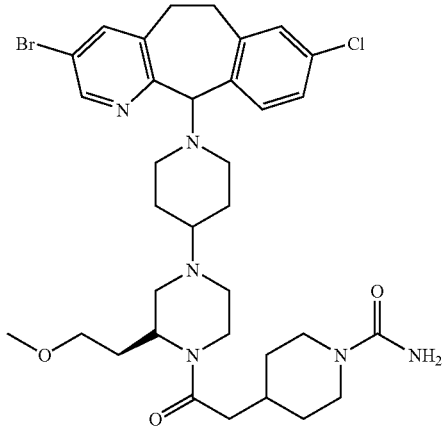

TABLE 1-continued
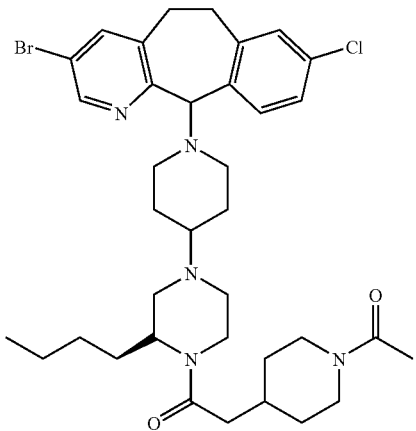
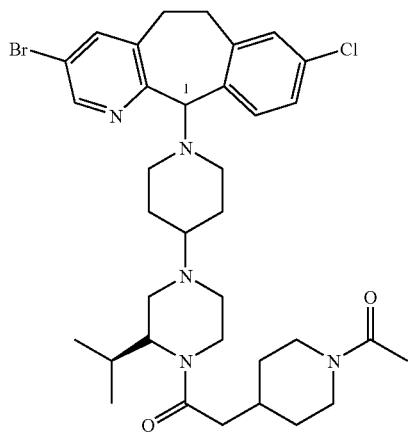
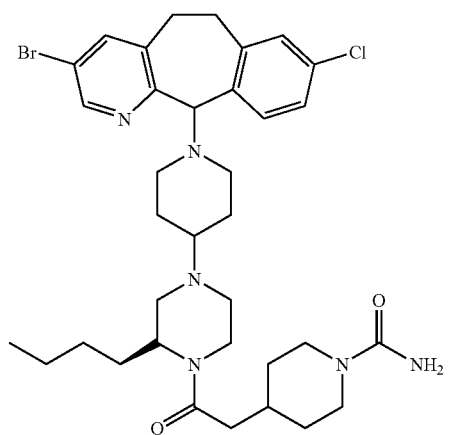
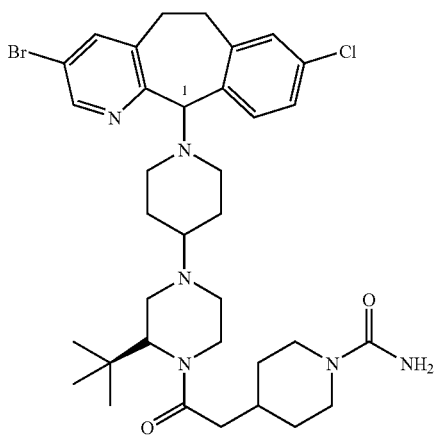
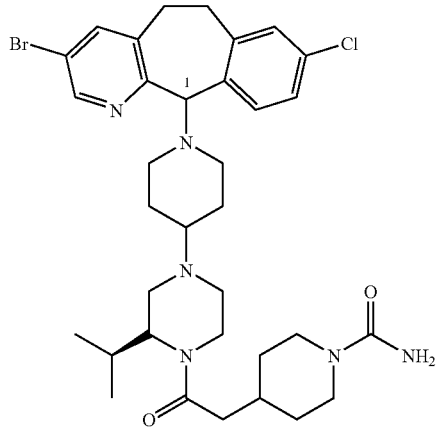
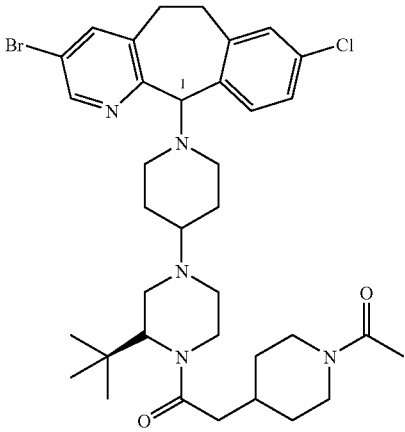

TABLE 1-continued
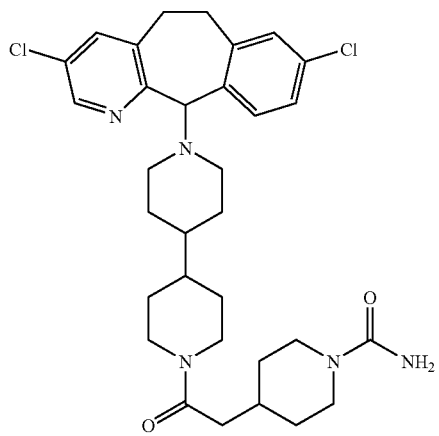
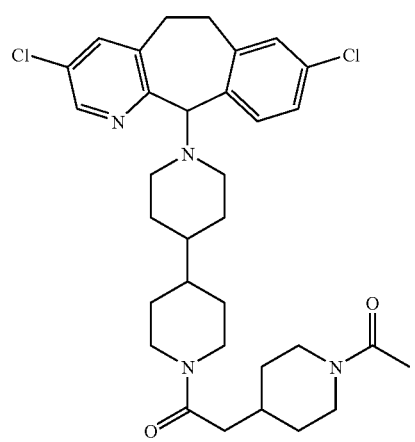
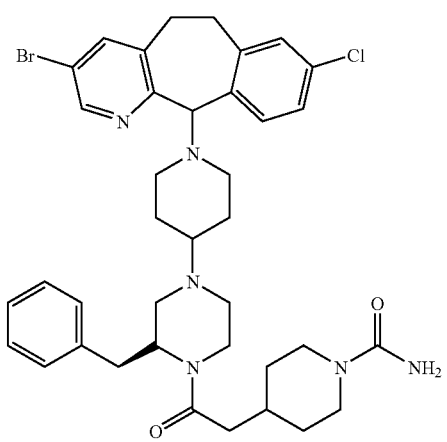
TABLE 1-continued
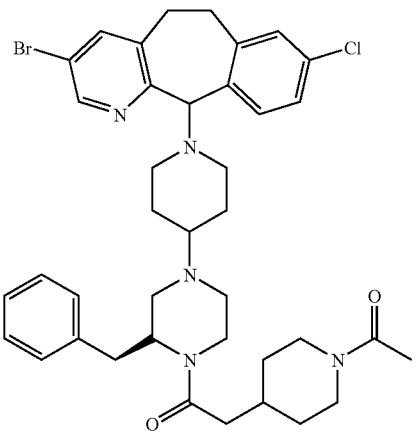
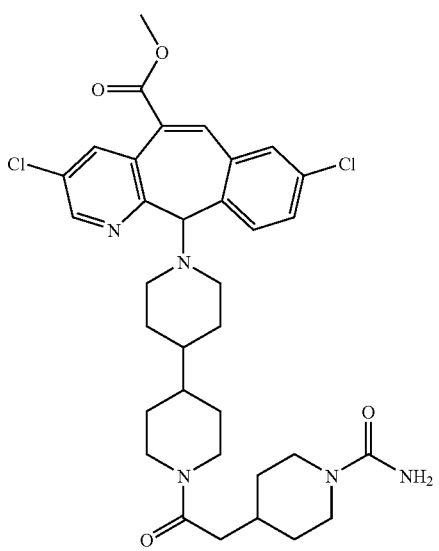
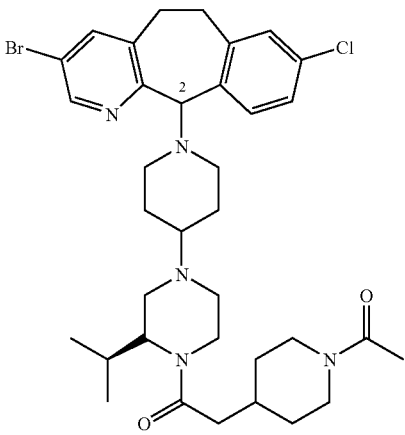

TABLE 1-continued

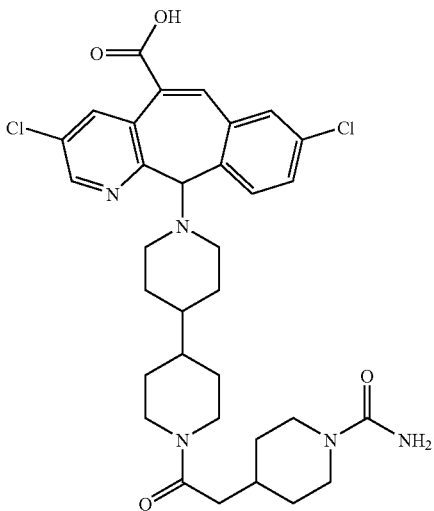

TABLE 1-continued

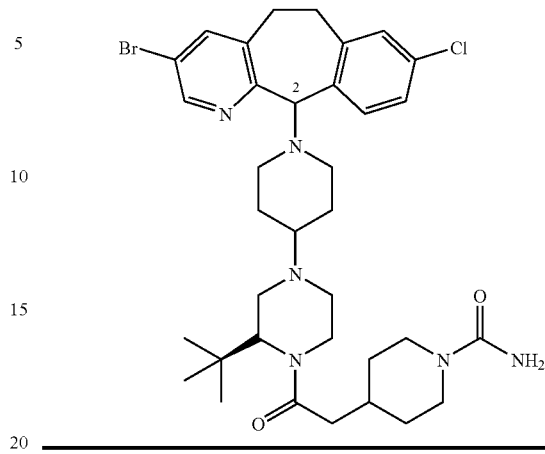

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched.

"Aryl" means an aromatic monocyclic or multicyclic ring system comprising about 6 to about 14 carbon atoms, preferably about 6 to about 10 carbon atoms. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, N-oxide of pyridyl, pyrazinyl, furanyl (furyl), thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,5-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Halogen" or "halo" means fluorine, chlorine, bromine, or iodine.

"Heterocyclyl" (or heterocycloalkyl) means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

"Ring system substituent" means a substituent attached to an aromatic or non-aromatic ring system which, for example, replaces an available hydrogen on the ring system. Ring system substituents may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $Y_1Y_2N-$, $Y_1Y_2N$-alkyl-, $Y_1Y_2NC(O)-$ and $Y_1Y_2NSO_2-$, wherein $Y_1$ and $Y_2$ may be the same or different and are independently selected from the group consisting of hydrogen, alkyl, aryl, and aralkyl. "Ring system substituent" also means a cyclic ring of 3 to 7 ring atoms of which 1-2 may be a heteroatom, attached to an aryl, heteroaryl, heterocyclyl or heterocyclenyl ring by simultaneously substituting two ring hydrogen atoms on said aryl, heteroaryl, heterocyclyl or heterocyclenyl ring. Non-limiting examples include:

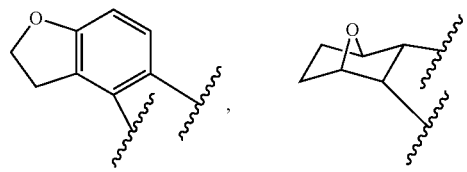

and the like.

The term "heteroaralkyl" or "heteroarylalkyl" means a heteroaryl-alkyl-group in which the heteroaryl and alkyl are as previously described. Preferred heteroarylalkyls comprise a lower alkyl group. Non-limiting examples of suitable heteroarylalkyl groups include pyridin-4-ylmethyl, thien-3-ylmethyl and the like. The bond to the parent moiety is through the alkyl.

The term "heterocyclylalkyl" means a heterocyclyl-alkyl-group in which the heterocyclyl and alkyl are as previously described. Preferred heterocyclylalkyls comprise a lower alkyl group. Non-limiting examples of suitable heterocyclylalkyl groups include piperidin-4-ylmethyl, pyrrolidin-3-ylmethyl and the like. The bond to the parent moiety is through the alkyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

As a general note to all the Tables that are attached hereto as well as to the Description, Examples and Schemes in this application, any open-ended nitrogen atom with unfulfilled valence in the chemical structures herein refers to NH, or in the case of a terminal nitrogen, $-NH_2$. Similarly, any open-ended oxygen atom or carbon atom with unfulfilled valence in the chemical structures herein refers to $-OH$ and any open-ended carbon atom with unfilled valence is appropriately filled with $-H$.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of Formula III or a salt and/or solvate thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting the type 3 17β-hydroxysteroid dehydrogenase and thus producing the desired therapeutic, ameliorative, inhibitory or preventative effect.

The compounds of formula I form salts which are also within the scope of this invention. Reference to a compound of formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the formula I may be formed, for example, by reacting a compound of formula I with an amount of acid or base, such as an equivalent amount, in a medium such as one in which the salt precipitates or in an aqueous medium followed by lyophilization. Acids (and bases) which are generally considered suitable for the formation of pharmaceutically useful salts from basic (or acidic) pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; in *The Orange Book* (Food & Drug Administration, Washington, D.C. on their website); and P. Heinrich Stahl, Camille G. Wermuth (Eds.), *Handbook of Pharmaceutical Salts: Properties, Selection, and Use*, (2002) Int'l. Union of Pure and Applied Chemistry, pp. 330-331. These disclosures are incorporated herein by reference thereto.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like.

Exemplary basic salts include ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis(dehydroabietyl)ethylenediamine), N-methyl-D-glucamines, N-methyl-D-glucamides, t-butyl amines, piperazine, phenylcyclohexylamine, choline, tromethamine, and salts with amino acids such as arginine, lysine and the like. Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of formula I, and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, positional isomers, racemates or prodrugs of the inventive compounds.

The invention also includes compounds of Formula I in isolated and purified form.

The compounds according to the invention have pharmacological properties; in particular, the compounds of Formula I can be inhibitors of type 3 17β-hydroxysteroid dehydrogenase. The novel compounds of Formula I are expected to be useful in the therapy of proliferative diseases associated with type 3 17β-hydroxysteroid dehydrogenase.

More specifically, the compounds of Formula I can be useful in the treatment or prevention of androgen or estrogen dependent diseases in a patient in need thereof, which comprises administering to said patient a therapeutically effective amount of at least one compound of formula I.

In another aspect, the invention provides a method of treating or preventing prostate cancer, and other androgen-dependent neoplasms, benign prostatic hyperplasia, prostatic intraepithelial neoplasia, androgenic alopecia (i.e. pattern baldness in both male and female patients), hirsutism, polycystic ovary syndrome and acne in a patient in need thereof, which comprises administering to said patient, a therapeutically effective amount of at least one compound of formula I.

In another aspect, the invention provides a method of treating or preventing androgen-dependent diseases in a patient in need thereof, comprising administering (concurrently or sequentially) to said patient an effective amount of at least one compound of formula I in combination or association with at least one anti-androgenic agent (i.e. agents that decrease androgen synthesis or activity).

This invention also provides a method of treating or preventing benign prostatic hyperplasia in a patient in need thereof, comprising administering (concurrently or sequentially) to said patient an effective amount of at least one compound of formula I in combination or association with at least one agent useful in the treatment or prevention of benign prostatic hyperplasia.

This invention also provides a method of treating or preventing hair loss in a patient in need thereof, comprising administering (concurrently or sequentially) to said patient an effective amount of at least one compound of formula I in combination or association with at least one agent useful in the treatment or prevention of alopecia, e.g., potassium channel agonists or 5α-reductase inhibitors.

This invention also provides a method of treating or preventing hair loss, comprising administering (concurrently or sequentially) to a patient in need thereof, an effective amount of a compound of formula I in combination with at least one potassium channel agonist e.g. minoxidil and KC-516, or 5α-reductase inhibitor, e.g., finasteride.

The invention also provides a method of treating or preventing proliferative diseases in a patient in need thereof, especially cancers (tumors), comprising administering (concurrently or sequentially) to said patient an effective amount of (1) at least one compound of formula I in combination or association with (2) an effective amount of at least one anti-cancer agent i.e., a chemotherapeutic agent, biological agent, and/or surgery, e.g., prostatectomy and/or radiation therapy.

Non-limiting examples of cancers (i.e. tumors) which may be inhibited or treated include, but are not limited to, lung cancer (e.g., lung adenocarcinoma), pancreatic cancers (e.g., pancreatic carcinoma such as, for example, exocrine pancreatic carcinoma), colon cancers (e.g., colorectal carcinomas, such as, for example, colon adenocarcinoma and colon adenoma), renal cancers, myeloid leukemias (for example, acute myelogenous leukemia (AML), thyroid follicular cancer, myelodysplastic syndrome (MDS), bladder carcinoma, epidermal carcinoma, melanoma, breast cancer and prostate cancer.

The method of treating proliferative diseases (cancer), according to this invention, includes a method for treating (inhibiting) the abnormal growth of cells, including transformed cells, in a patient in need of such treatment, by administering, concurrently or sequentially, an effective amount of at least one compound of this invention and an effective amount of at least one chemotherapeutic agent, biological agent, surgery (e.g. prostatectomy) and/or radiation. Abnormal growth of cells means, for example, cell growth independent of normal regulatory mechanisms (e.g., contact inhibition or apoptosis), including the abnormal growth of: (1) tumor cells (tumors) expressing an activated ras oncogene; (2) tumor cells in which the ras protein is activated as a result of oncogenic mutation in another gene; and (3) benign and malignant cells of other proliferative diseases.

In its embodiments, the present invention includes methods for treating or inhibiting tumor growth in a patient in need of such treatment, by administering, concurrently or sequentially, (1) an effective amount of at least one compound of this invention and (2) an effective amount of at least one antineoplastic/microtubule agent, biological agent, and/or surgery (e.g. prostatectomy) and/or radiation therapy. Examples of tumors which may be treated include, but are not limited to, epithelial cancers, e.g., prostate cancer, lung cancer (e.g., lung adenocarcinoma), pancreatic cancers (e.g., pancreatic carcinoma such as, for example, exocrine pancreatic carcinoma), breast cancers, renal cancers, colon cancers (e.g., colorectal carcinomas, such as, for example, colon adenocarcinoma and colon adenoma), ovarian cancer, and bladder carcinoma. Other cancers that can be treated include melanoma, myeloid leukemias (for example, acute myelogenous leukemia), sarcomas, thyroid follicular cancer, and myelodysplastic syndrome.

As used herein the following terms have the following meanings unless indicated otherwise:

"Antineoplastic agent" means a chemotherapeutic agent effective against cancer;

"Concurrently" means (1) simultaneously in time, or (2) at different times during the course of a common treatment schedule; and "Sequentially" means (1) administration of one component of the method ((a) compound of the invention, or (b) antineoplastic agent and/or radiation therapy) followed by administration of the other component; after administration of one component, the second component can be administered substantially immediately after the first component, or the second component can be administered after an effective time period after the administration of the first component; the effective time period is the amount of time given for realization of maximum benefit from the administration of the first component.

A preferred dosage is about 0.001 to 500 mg/kg of body weight/day of the compound of Formula I. An especially preferred dosage is about 0.01 to 25 mg/kg of body weight/day of a compound of Formula I, or a pharmaceutically acceptable salt or solvate of said compound.

Certain useful combination/association agents are described below:

Chemotherapeutic Agents

Classes of compounds that can be used as the chemotherapeutic agent (antineoplastic agent) include: alkylating agents, antimetabolites, natural products and their derivatives, hormones and steroids (including synthetic analogs), and synthetics. Non-limiting examples of compounds within these classes are:

Alkylating agents (including nitrogen mustards, ethylenimine derivatives, alkyl sulfonates, nitrosoureas and triazenes): Uracil mustard, Chlormethine, Cyclophosphamide (Cytoxan®), Ifosfamide, Melphalan, Chlorambucil, Pipobroman, Triethylenemelamine, Triethylenethiophosphoramine, Busulfan, Carmustine, Lomustine, Streptozocin, Dacarbazine, and Temozolomide.

Antimetabolites (including folic acid antagonists, pyrimidine analogs, purine analogs and adenosine deaminase inhibitors): Methotrexate, 5-Fluorouracil, Floxuridine, Cytarabine, 6-Mercaptopurine, 6-Thioguanine, Fludarabine phosphate, Pentostatine, and Gemcitabine.

Natural products and their derivatives (including vinca alkaloids, antitumor antibiotics, enzymes, lymphokines and epipodophyllotoxins): Vinblastine, Vincristine, Vindesine, Bleomycin, Dactinomycin, Daunorubicin, Doxorubicin, Epirubicin, Idarubicin, paclitaxel (paclitaxel is commercially available as Taxol® and is described in more detail below in the subsection entitled "Microtubule Affecting Agents"), Mithramycin, Deoxycoformycin, Mitomycin-C, L-Asparaginase, Interferons-α and β (especially IFN-α), Etoposide, and Teniposide.

Hormonal agents and steroids (including synthetic analogs): 17α-Ethinylestradiol, Diethylstilbestrol, Testosterone, Prednisone, Fluoxymesterone, Dromostanolone propionate, Testolactone, Megestrolacetate, Tamoxifen, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin and Zoladex.

Synthetics (including inorganic complexes such as platinum coordination complexes): Cisplatin, Carboplatin, Hydroxyurea, Amsacrine, Procarbazine, Mitotane, Mitoxantrone, Levamisole, Navelbene, CPT-11, Anastrazole, Letrazole, Capecitabine, Ralozifine, Droloxifine and Hexamethylmelamine.

Non-limiting examples of biological agents useful in the methods of this invention include but are not limited to, interferon-α, interferon-β and gene therapy.

Microtubule Affecting Agents

As used herein, a microtubule affecting agent is a compound that interferes with cellular mitosis, i.e., having an anti-mitotic effect, by affecting microtubule formation and/or action. Such agents can be, for instance, microtubule stabilizing agents or agents which disrupt microtubule formation.

Non-limiting examples of microtubule affecting agents useful in the invention include allocolchicine (NSC 406042), Halichondrin B (NSC 609395), colchicine (NSC 757), colchicine derivatives (e.g., NSC 33410), dolastatin 10 (NSC 376128), maytansine (NSC 153858), rhizoxin (NSC 332598), paclitaxel (Taxol®, NSC 125973), Taxol® derivatives (e.g., derivatives (e.g., NSC 608832), thiocolchicine (NSC 361792), trityl cysteine (NSC 83265), vinblastine sulfate (NSC 49842), vincristine sulfate (NSC 67574), epothilone A, epothilone, discodermolide, estramustine, nocodazole, MAP4, and the like.

Particularly preferred agents are compounds with paclitaxel-like activity. These include, but are not limited to, paclitaxel and paclitaxel derivatives (paclitaxel-like compounds) and analogues. Paclitaxel and its derivatives are available commercially. More specifically, the term "paclitaxel" as used herein refers to the drug commercially available as Taxol®.

Examples of such agents include, but are not limited to, inhibitors of 5α-reductase type 1 and/or type 2, e.g. finasteride, SKF105,657, LY191,704, LY320,236, dutasteride, flutamide, nicalutamide, bicalutamide, LHRH agonists e.g. leuprolide and zoladex, LHRH antagonists, e.g. abarelix and cetrorelix, inhibitors of 17α-hydroxylase/C17-20 lyase, e.g. YM116, CB7630 and liarozole; inhibitors of 17β-hydroxysteroid dehydrogenase type 5 and/or other 17β-hydroxysteroid dehydrogenase/17β-oxidoreductase isoenzymes, e.g. EM-1404.

Types of androgen or estrogen dependent diseases include, but are not limited to, prostate cancer, benign prostatic hyperplasia, prostatic intraepithelial neoplasia, acne, seborrheas, hirsutism, androgenic alopecia, precocious puberty, adrenal hyperplasia, and polycystic ovarian syndrome, breast cancer, endometriosis and leiomyoma.

Examples of agents useful in the treatment or prevention of benign prostatic hyperplasia include, but are not limited to, α-1 adrenergic antagonists, e.g. tamsulosin and terazosin.

The pharmacological properties of the compounds of this invention may be confirmed by a number of pharmacological assays. The exemplified pharmacological assays which are described later have been carried out with the compounds according to the invention and their salts.

This invention is also directed to pharmaceutical compositions which comprise at least one compound of Formula I, or a pharmaceutically acceptable salt or solvate of said compound and at least one pharmaceutically acceptable carrier.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 500 mg/day, preferably 1 mg/day to 200 mg/day, in two to four divided doses.

The chemotherapeutic agent and/or radiation therapy can be administered in combination or association with the compounds of the present invention according to the dosage and administration schedule listed in the product information sheet of the approved agents, in the *Physicians Desk Reference* (PDR) as well as therapeutic protocols well known in the art. Table A below gives ranges of dosage and dosage regimens of some exemplary chemotherapeutic agents useful in the methods of the present invention. It will be apparent to those skilled in the art that the administration of the chemotherapeutic agent and/or radiation therapy can be varied depending on the disease being treated and the known effects of the chemotherapeutic agent and/or radiation therapy on that disease. Also, in accordance with the knowledge of the skilled clinician, the therapeutic protocols (e.g., dosage amounts and times of administration) can be varied in view of the observed effects of the administered chemotherapeutic agents (i.e., antineoplastic agent or radiation) on the patient, and in view of the observed responses of the disease to the administered therapeutic agents.

TABLE A

Exemplary Chemotherapeutic Agents Dosage and Dosage Regimens

| | |
|---|---|
| Cisplatin: | 50-100 mg/m² every 4 weeks (IV)* |
| Carboplatin: | 300-360 mg/m² every 4 weeks (IV) |
| Taxotere: | 60-100 mg/m² every 3 weeks (IV) |
| Gemcitabine: | 750-1350 mg/m2 every 3 weeks (IV) |
| Taxol: | 65-175 mg/m2 every 3 weeks (IV) |

*(IV)-intravenously

Anti-androgenic agents, anti-benign prostatic hyperplasia agents, potassium channel agonists and biological agents can be administered in association with the compounds of the present invention according to the dosage and administration schedule listed in the product information sheet of the approved agents, in the *Physicians Desk Reference* (PDR) as well as therapeutic protocols well known in the art. It will be apparent to those skilled in the art that the administration of the agents can be varied depending on the disease being treated and the known effects of the agents on that disease. Also, in accordance with the knowledge of the skilled clinician, the therapeutic protocols (e.g., dosage amounts and times of administration) can be varied in view of the observed effects of the administered agents on the patient, and in view of the observed responses of the disease to the administered therapeutic agents.

Another aspect of this invention is a kit comprising a therapeutically effective amount of at least one compound of Formula I, or a pharmaceutically acceptable salt or solvate of said compound and a pharmaceutically acceptable carrier, vehicle or diluent.

Yet another aspect of this invention is a kit comprising an amount of at least one compound of Formula I, or a pharmaceutically acceptable salt or solvate of said compound and an amount of at least one additional agent listed above, wherein the amounts of the two or more ingredients result in desired therapeutic effect.

The above-described kits may contain the said ingredients in one or more containers within said kit.

The invention disclosed herein is exemplified by the following preparations and examples which should not be construed to limit the scope of the disclosure. Alternative mechanistic pathways and analogous structures will be apparent to those skilled in the art.

Where NMR data are presented, $^1$H spectra were obtained on either a Varian VXR-200 (200 MHz, $^1$H), Varian Gemini-300 (300 MHz) or XL-400 (400 MHz) and are reported as ppm down field from Me$_4$Si with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm×7 mm ID; gradient flow: 0 min-10% CH$_3$CN, 5 min-95% CH$_3$CN, 7 min-95% CH$_3$CN, 7.5 min-10% CH$_3$CN, 9 min-stop. The retention time and observed parent ion are given.

The following solvents and reagents may be referred to by their abbreviations in parenthesis:
Thin layer chromatography: TLC
ethyl acetate: AcOEt or EtOAc
trifluoroacetate: TFA
triethylamine: TEA
butoxycarbonyl: n-Boc or Boc
nuclear magnetic resonance spectroscopy: NMR
liquid chromatography mass spectrometry: LCMS
high resolution mass spectrometry: HRMS
milliliters: mL
millimoles: mmol
microliters: μl
grams: g
milligrams: mg
room temperature or rt (ambient): about 25° C.

EXAMPLES

Compounds of formula (I) may be produced by processes known to those skilled in the art. Illustrative procedures are shown in the representative Schemes, preparations and Examples below. These schemes, preparations and examples should not be construed to limit the scope of the disclosure. Alternative mechanistic pathways and analogous structures may be apparent to those skilled in the art. Some of the compounds made by these processes are listed in Table 1. As stated earlier, all kinds of isomeric forms of the compounds are considered to be within the scope of this invention.

The piperidine-piperazine core is added to an appropriate chloride. Deprotection and coupling with N-BOC piperidine acetic acid, followed by deprotection and acylation, gives the desired product (Scheme 1).

Scheme 1

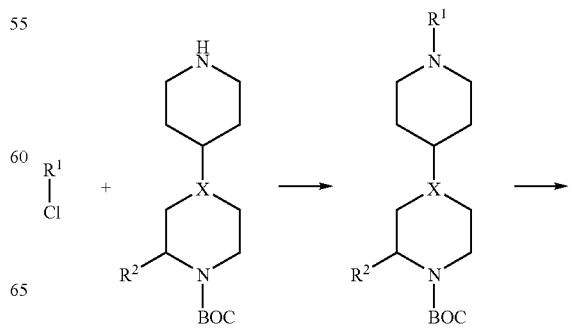

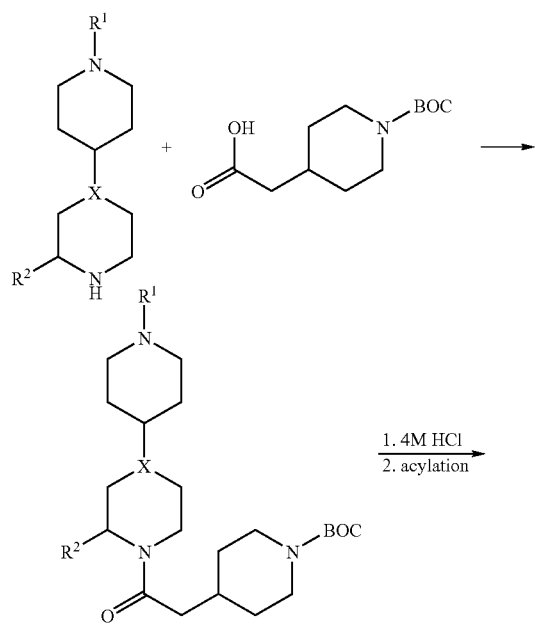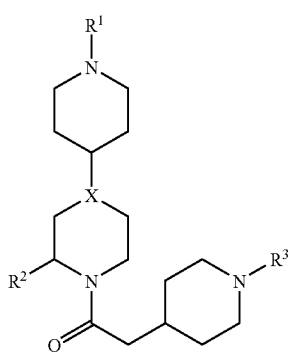
X = CH or N
Alternatively, the desired piperidine-piperazine intermediate in Scheme 1 can be prepared from an appropriate piperidone (Scheme 2).
Scheme 2
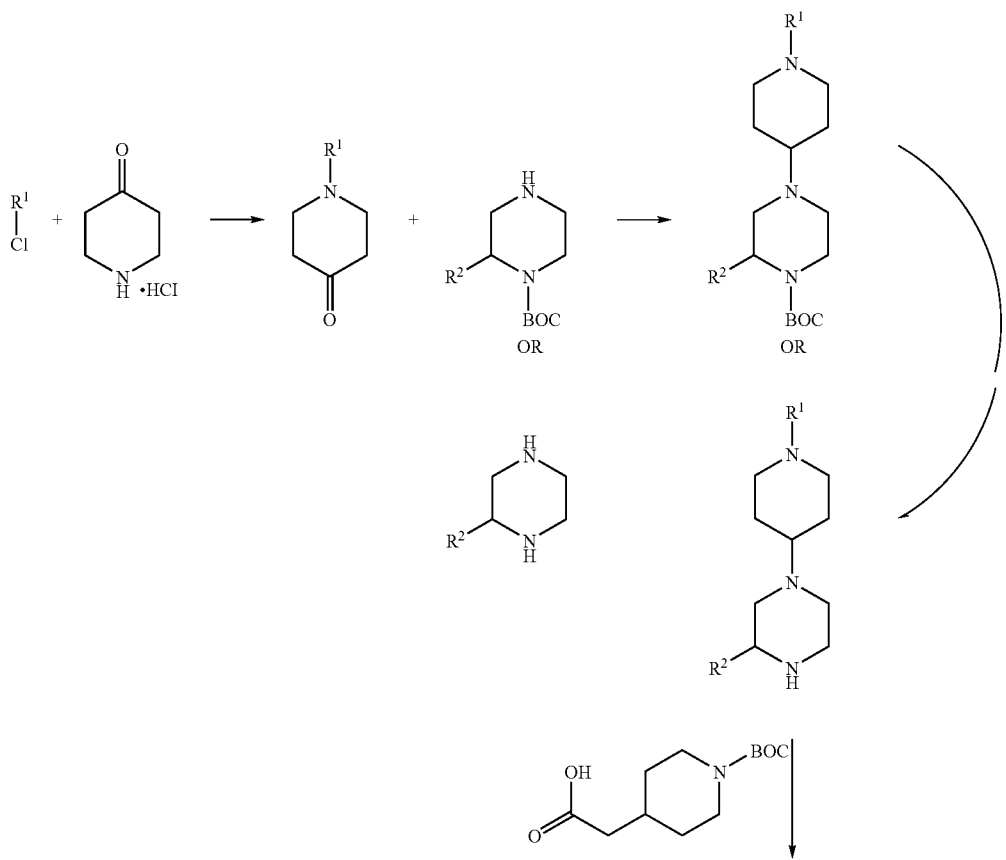

-continued

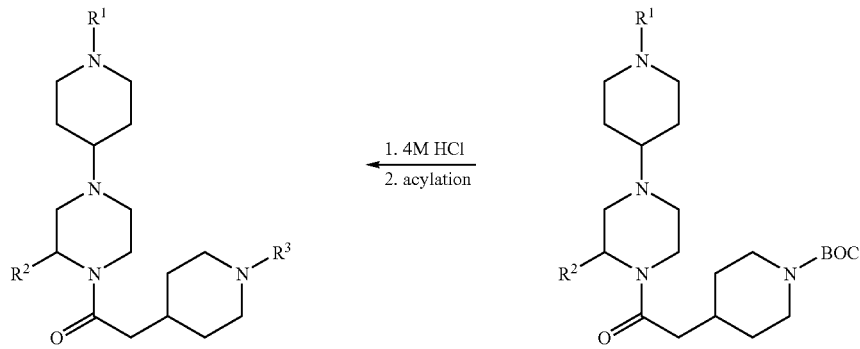

Alternatively, the piperidine-piperazine-piperidine core is added to an appropriate chloride to give the desired product, followed by deprotection and acylation (Scheme 3).

Alternatively, the piperazine-piperidine core is added to an appropriate piperidone to give the desired product (Scheme 4).

Scheme 3

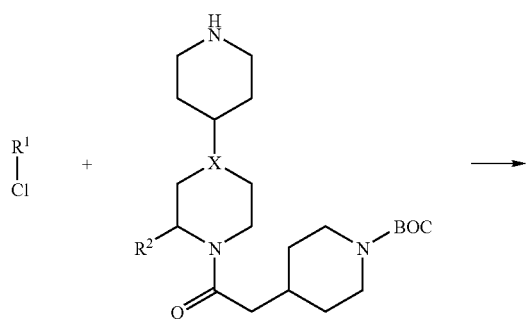

Scheme 4

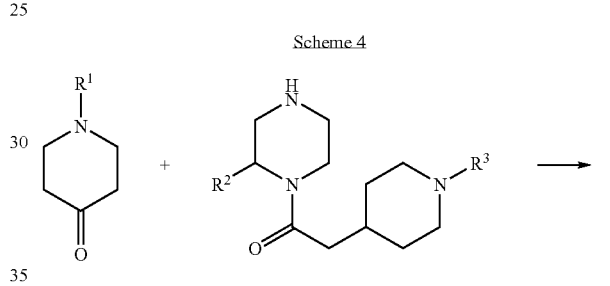

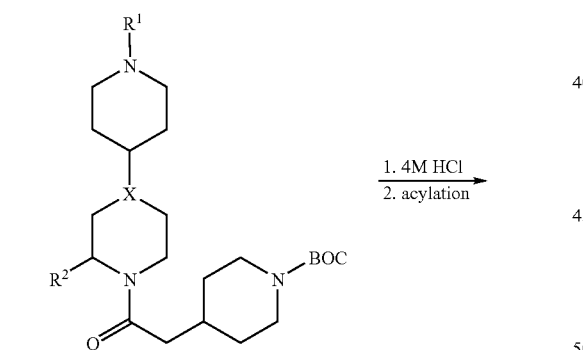

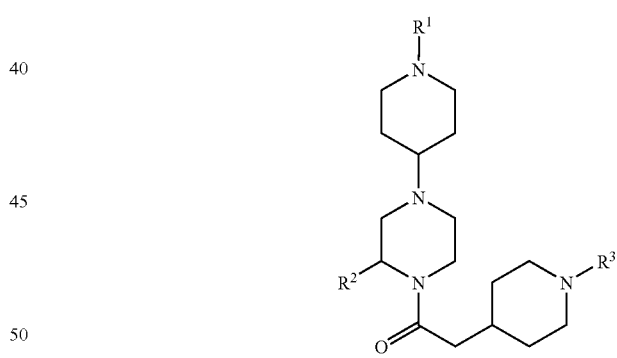

The synthesis of desired chlorides can be accomplished by the reduction of an appropriate ketone (Scheme 5). The resulting alcohol is then converted to the requisite chloride under standard conditions. (U.S. Pat. No. 5,719,148).

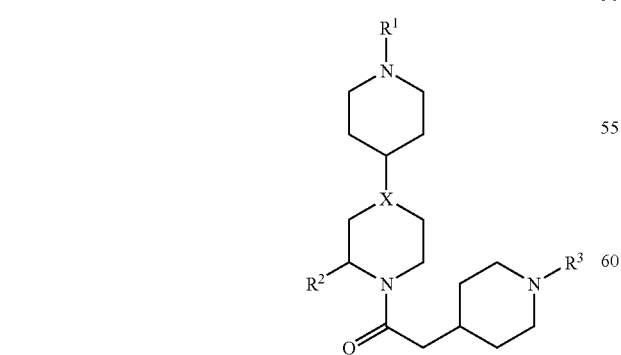

X = CH or N

Scheme 5

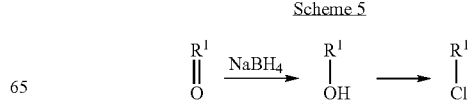

The substituted piperazines can be prepared through the reduction of commercially available diketopiperazines or alternatively from the desired amino acids (Scheme 6).

Scheme 6

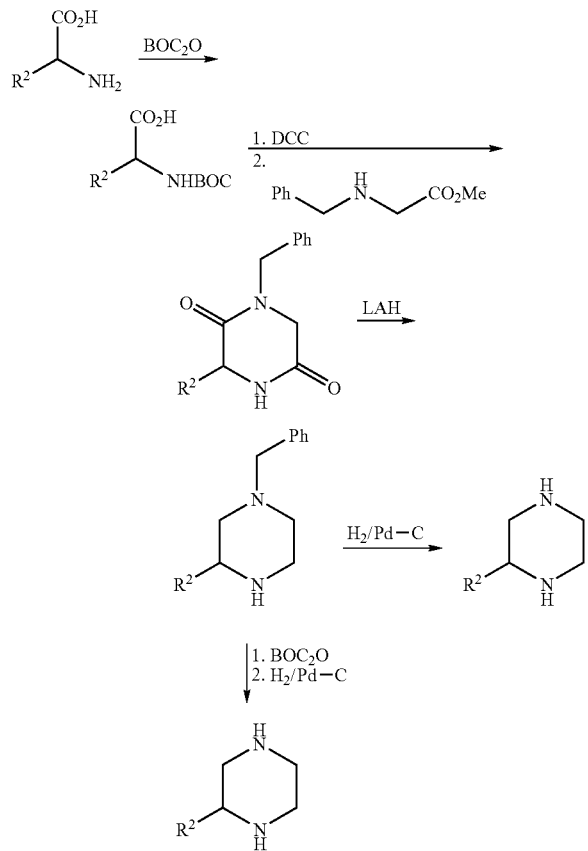

The N-BOC or N-acyl piperidine acetic acid can be prepared as described previously through the reduction of 4-pyridine acetic acid (Scheme 7).

Scheme 7

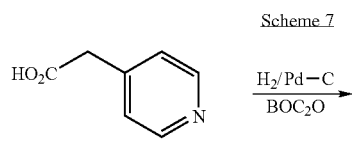

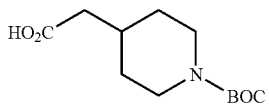

Preparative Example 1

To a solution of DCC (43.2 mL, 1.0 M in CH$_2$Cl$_2$, 1.0 eq.) in CH$_2$Cl$_2$ (200 mL) at 0° C. was added N-t-BOC-L-leucine (10 g, 43.2 mmol). To the resulting slurry was added ethyl N-benzylglycinate (8.1 mL, 1.0 eq.) over 15 minutes. The resulting solution was stirred at 0° C. for 2 hours and room temperature 1 hour, filtered and the concentrated to give a colorless oil (20.7 g, LCMS: MH$^+$=407). The intermediate was dissolved in CH$_2$Cl$_2$ (150 mL) through which HCl (g) was bubbled for 4 hours. The solution was purges with N$_2$ and concentrated under reduced pressure. The residue was neutralized with saturated NaHCO$_3$ and extracted with EtOAc (3×200 mL). The combined organics were washed with water, dried over Na$_2$SO$_4$, filtered and concentrated to give a white solid which was used without further purification (11.3 g, 100% yield). LCMS: MH$^+$=261.

Preparative Example 2-4

By essentially the same procedure set forth in Preparative Example 1 only substituting the amino acids from Table 1, Column 2, the title compounds in Table 1A, Column 3, were prepared:

TABLE 1A

| Prep. Ex. | Column 2 | Column 3 | DATA |
|---|---|---|---|
| 2 | | | LCMS: MH$^+$ = 261 |

TABLE 1A-continued

| Prep. Ex. | Column 2 | Column 3 | DATA |
|---|---|---|---|
| 3 | (structure: BOC-protected tert-leucine) | (structure: 1-benzyl-3-tert-butyl-2,5-piperazinedione) | LCMS: MH+ = 261 |
| 4 | (structure: BOC-protected O-methyl homoserine) | (structure: 1-benzyl-3-(2-methoxyethyl)-2,5-piperazinedione) | — |

Preparative Example 5

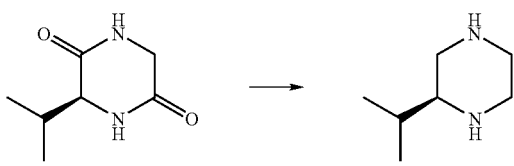

To a solution of (S)-3-isopropyl-2,5-piperazinedione (5.0 g, 32 mmol) in THF (100 mL) at 0° C. was added LAH (137 mL, 1.0 M in THF, 4.3 eq.) dropwise. After the addition was complete, the resulting solution was heated to reflux overnight. The reaction mixture was cooled to room temperature and quenched by the slow, sequential addition of water (5.23 mL), 1N NaOH (5.23 mL), and water (5.23 mL). The resulting slurry was diluted with EtOAc and filtered through a plug of Celite. The residue was washed with EtOAc (4×100 mL) and the combined organics concentrated under reduced pressure. The crude product was purified by flash chromatography using a gradient of 5% MeOH, 10% MeOH, 5% (10% NH$_4$OH) in MeOH, 10% (10% NH$_4$OH) in MeOH, and 20% (10% NH$_4$OH) in MeOH in CH$_2$Cl$_2$ to give a pale yellow solid (3.03 g, 74% yield). LCMS: MH+=129.

Preparative Example 6-11

By essentially the same procedure set forth in Preparative Example 5 only substituting the piperazinediones from Table 2, Column 2, the title compounds in Table 2, Column 3 were prepared:

TABLE 2

| Prep. Ex. | Column 2 | Column 3 | DATA |
|---|---|---|---|
| 6 | (structure: 1-benzyl-3-isobutyl-2,5-piperazinedione) | (structure: 1-benzyl-3-isobutylpiperazine) | LCMS: MH+ = 233 |

TABLE 2-continued

| Prep. Ex. | Column 2 | Column 3 | DATA |
|---|---|---|---|
| 7 | | | LCMS: MH⁺ = 233 |
| 8 | | | LCMS: MH⁺ = 233 |
| 9 | | | FABMS: MH⁺ = 235 |
| 10 | | | LCMS: MH⁺ = 143 |
| 11 | | | — |

Preparative Example 12

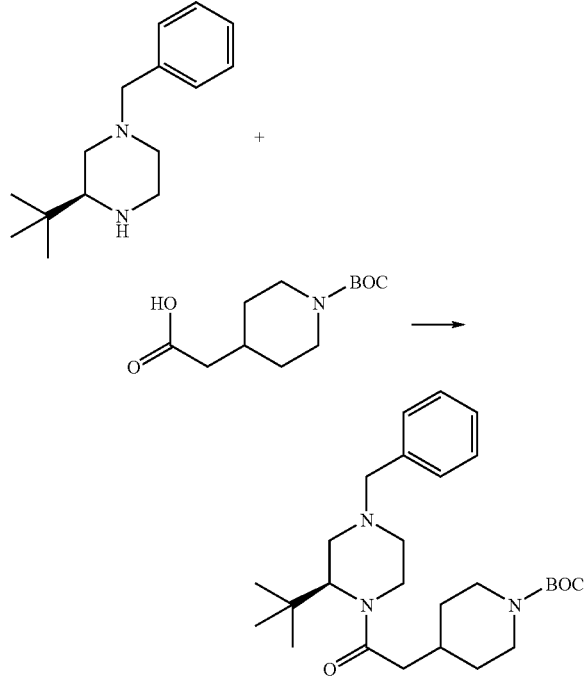

To a solution of N-Boc-4-piperidineacid acid (prepared as described in U.S. Pat. No. 5,874,442; 35.0 g, 144 mmol) and TEA (20.0 mL, 1.0 eq.) in toluene (100 mL) at 0° C. was added trimethylacetyl chloride (17.7 mL, 1.0 eq.). The resulting slurry was stirred at 0° C. 1.5 hours before adding the title compound from Preparative Example 8 (33.5 g, 151 mmol, 1.05 eq.) in toluene (100 mL) and the resulting solution was warmed to room temperature and stirred overnight. The reaction mixture was neutralized by the addition of 1N NaOH and extracted with EtOAc. The combined organics were dried over $Na_2SO_4$, filtered, and concentrated. The crude product was purified by flash chromatography using a 50:50 EtOAc:Hexane solution as eluent (34.4 g, 51% yield). LCMS: $MH^+$=458.

Preparative Example 13

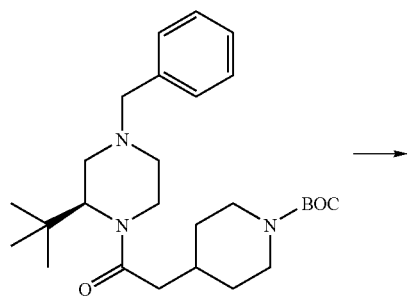

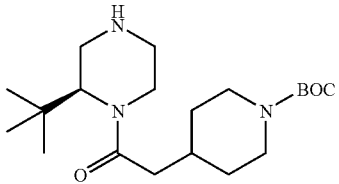

To a solution of the title compound from Preparative Example 12 (34.0 g, 74.3 mmol) in absolute EtOH (600 mL) was added 10% Pd—C (35.0 g, wet, 50%) and $NH_4HCO_2$ (94 g, 10 eq.). The reaction mixture was heated to reflux for 3 hours, cooled to room temperature, filtered through a plug of Celite and concentrated under reduced pressure. The residue was diluted with EtOAc and washed sequentially with $H_2O$, 1N NaOH, $H_2O$, and brine. The organics were dried over $Na_2SO4$, filtered, and concentrated in vacuo. The crude product was purified by flash chromatography using a 5% (10% $NH_4OH$ in MeOH) in $CH_2Cl_2$ to 10% (10% $NH_4OH$ in MeOH in $CH_2Cl_2$ as eluent (20 g, 74% yield). LCMS: $MH^+$=368.

Preparative Example 14

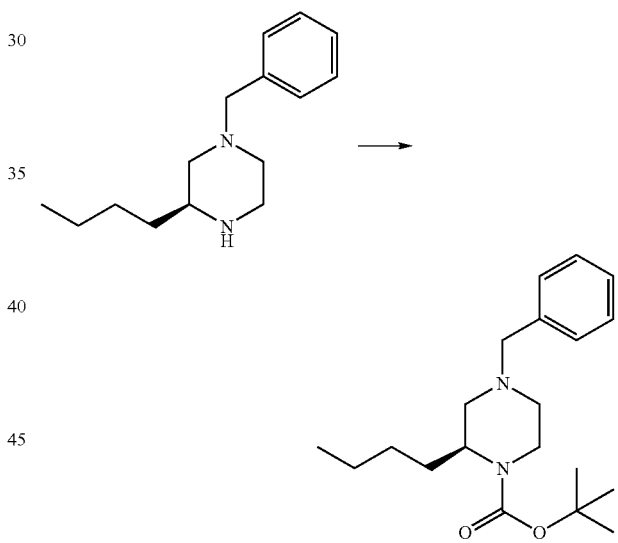

To a solution of the title compound from Preparative Example 7 (8.2 g, 31.5 mmol) in $CH_2Cl_2$ (300 mL) was added $(BOC)_2O$ (7.5 g, 1.02 eq.). The resulting solution was stirred at room temperature overnight. The reaction quenched by the addition of saturated $NaHCO_3$ and separated. The organic layer was washed with brine, dried over $Na_2SO_4$, filtered, and concentrated under reduced pressure. The crude product was purified by flash chromatography using a 10% EtOAc in hexanes solution as eluent (10.6 g, 99% yield). LCMS: $MH^+$=333.

Preparative Example 15

By essentially the same procedure set forth in Preparative Example 14, only substituting the title compound from Preparative Example 9 in Table 3, Column 2, the title compounds in Table 3, Column 3 was prepared:

TABLE 3

| Prep. Ex. | Column 2 | Column 3 | DATA |
|---|---|---|---|
| 15 | | | LCMS: MH⁺ = 335 |

Preparative Example 16

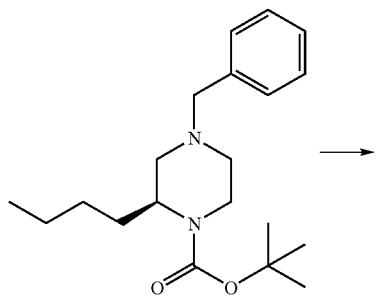

→

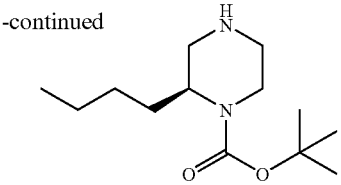
-continued

A solution of the title compound from Preparative Example 14 (10.4 g, 31.3 mmol) and 10% Pd/C (1.95 g) in EtOH (130 mL) was hydrogenated on a Parr apparatus at 50 psi overnight. The reaction mixture was filtered through Celite and the filtrate concentrated in vacuo to give the product as a colorless oil (6.93 g, 91% yield) which was used without further purification. LCMS: MH⁺=243.

Preparative Examples 17-20

By essentially the same procedure set forth in Preparative Example 16 only substituting compounds from Table 4, Column 2, the title compounds in Table 4, Column 3 were prepared:

TABLE 4

| Prep. Ex. | Column 2 | Column 3 | DATA |
|---|---|---|---|
| 17 | | | LCMS: MH⁺ = 245 |

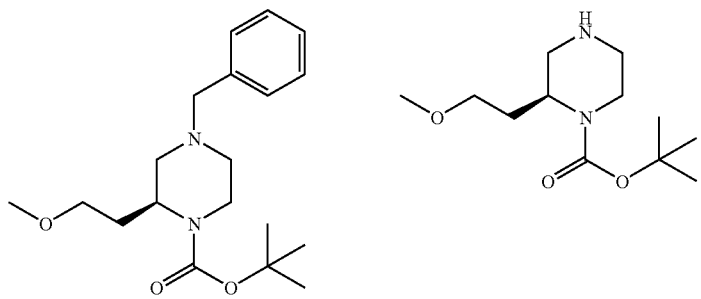

TABLE 4-continued

| Prep. Ex. | Column 2 | Column 3 | DATA |
|---|---|---|---|
| 18 | | | LCMS: MH+ = 368 |
| 19 | | | LCMS: MH+ = 356 |
| 20 | | | LCMS: MH+ = 368 |

Preparative Example 21

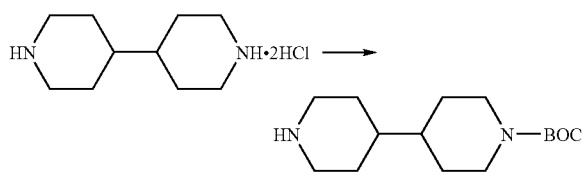

4,4'-Bipiperidine (17.5 g, 72.55 mmol) was dissolved in H$_2$O (70 mL), treated with 5 N NaOH to pH 8-9, and diluted to 400 mL with EtOH. To the stirred mixture at room temperature was added di-t-butyl dicarbonate (16.8 g, 76.96 mmol) in 200 mL of EtOH in one portion. The reaction mixture was treated with 5 N NaOH periodically to pH 8-9. After 5 hours, the mixture was concentrated. The residue was dissolved in 500 mL of 1:1 H$_2$O:Et$_2$O and the PH was adjusted to 12 with 5 N NaOH. The aqueous phase was extracted with Et$_2$O and combined organic phase was washed with brine, 5% aq. citric acid. The citric acid washing solution was adjusted to PH 12-13 with 5 N NaOH and extracted with 250 mL of Et$_2$O 3 times. The combined Et$_2$O was washed with brine, dried over MgSO$_4$ and concentrated under vacuum to give the desired product (8.61 g, 44.2% yield). FABMS: MH+=269.

Preparative Example 22

Step A

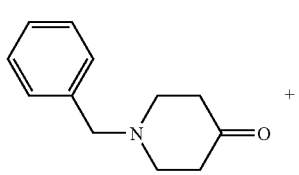

-continued

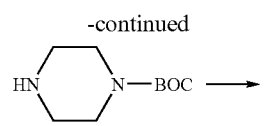

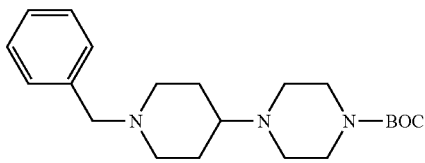

1-Benzyl-4-piperidone (4.00 g, 21.13 mmol), t-BOC-piperazine (3.94 g, 21.14 mmol) and Ti(OiPr)$_4$ (7.5 g, 26.38 mmol) were stirred at r.t. under N$_2$ in dry CH$_2$Cl$_2$ (8 mL) overnight. To the reaction absolute EtOH (60 mL) was added, followed by NaCNBH$_3$ (1.32 g, 21 mmol). The mixture was stirred at r.t. for 6 hrs, diluted with 10 mL of EtOAc, added 20 g filter celite, 100 mL of ice-cold H$_2$O and stirred for 1 hr. The mixture was then filtered and cake was washed with CH$_2$Cl$_2$. The combined CH$_2$Cl$_2$ was washed with brine, dried over Na$_2$SO$_4$, filtered, and concentrated. The crude product was purified by flash chromatography using a 3-5% MeOH in CH$_2$Cl$_2$ to yield a colorless solid (2.45 g, 32% yield). FABMS: MH$^+$=360.

Step B

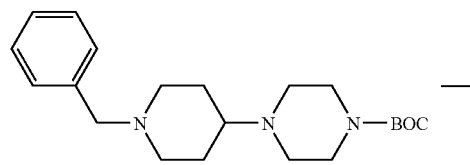

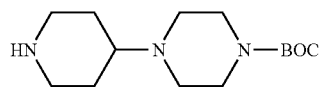

To a solution of the title compound from Preparative Example 22, Step A (1.29 g, 3.59 mmol) and Pd/C (0.4 g, 10%) in MeOH (25 mL) was added 96% HCOOH (1 mL, 5.0 eq.). The resulting mixture was stirred at r.m. overnight and filtered through a celite pad and washed with MeOH. The combined filtrate was concentrated to syrup, 5 mL of water was added to it and adjusted to PH 12 with 15% NaOH. The mixture was extracted with EtOAc (30 mL) twice and EtOH:CH$_2$Cl$_2$ 1:4 (50 mL) twice. The combined organics were dried over Na$_2$SO$_4$, filtered, and concentrated to yield a colorless solid (0.91 g, 94% yield). FABMS: MH$^+$=270.

Preparative Example 23

Step A

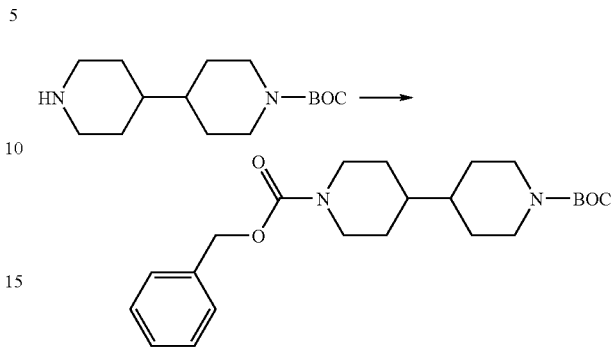

To a solution of the title compound from Preparative Example 21 (2.66 g, 9.93 mmol) in 40 mL of 50% aq. MeOH was added Na$_2$CO$_3$ (2.1 g). followed by dropwise addition of CbzCl (1.7 mL, 11.9 mmol). The resulting mixture was stirred at 0° C. for 1 hr. and r.t. for 24 hrs. 100 mL of distilled water was added to the reaction and the mixture was extracted with EtOAc (100 mL) twice. The crude product was purified by flash chromatography using a 1% MeOH in CH$_2$Cl$_2$ to yield a white solid (2.97 g). FABMS: MH$^+$=403.

Step B

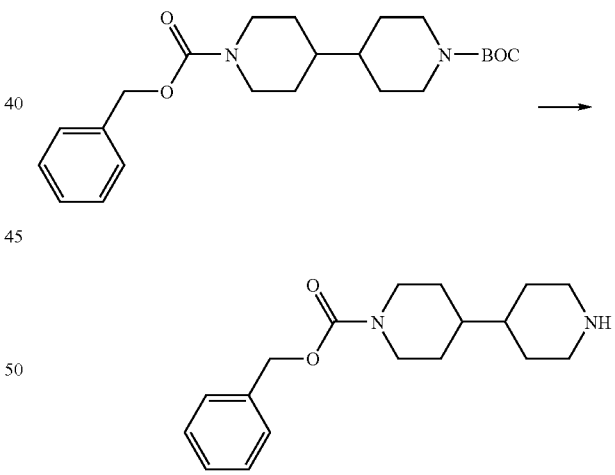

To a solution of the title compound from Preparative Example 23, STEP A (1.3 g, 3.23 mmol) in CH$_2$Cl$_2$ (40 mL) at 0° C. was added dropwise TFA (31 mL) over 10 min. The resulting mixture was stirred at 0-5° C. for 2 hrs, then concentrated under reduced pressure. The residue was dissolved in CH$_2$Cl$_2$/H$_2$O, adjusted pH to 12 by the addition of 5N NaOH, separated, extracted aqueous layer with CH$_2$Cl$_2$. The combined organics were dried over Na$_2$SO$_4$, filtered and concentrated to give a white solid (0.885 g) which was used without further purification. FABMS: MH$^+$=303.

Step C

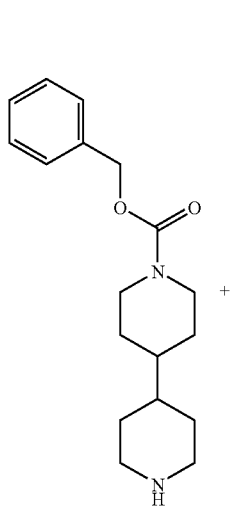

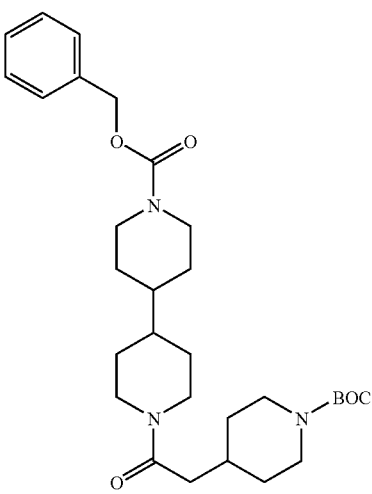

A solution of the title compound from Preparative Example 23, STEP B, N-Boc-4-piperidineacid acid (prepared as described in U.S. Pat. No. 5,874,442; 0.1.24 g), DEC (0.86 g), HOBt (0.6 g), and NMM (0.75 mL) in anhydrous DMF (20 mL) was stirred at room temperature for 24 hrs. The reaction was quenched by the addition of 1N NaOH and extracted with $CH_2Cl_2$. The combined organics were dried over $Na_2SO_4$, filtered, and concentrated. The crude product was purified by flash chromatography using a 10% acetone in hexane solution as eluent to give the desired product (1.75 g, 98% yield); FABMS: $MH^+$=528.

Step D

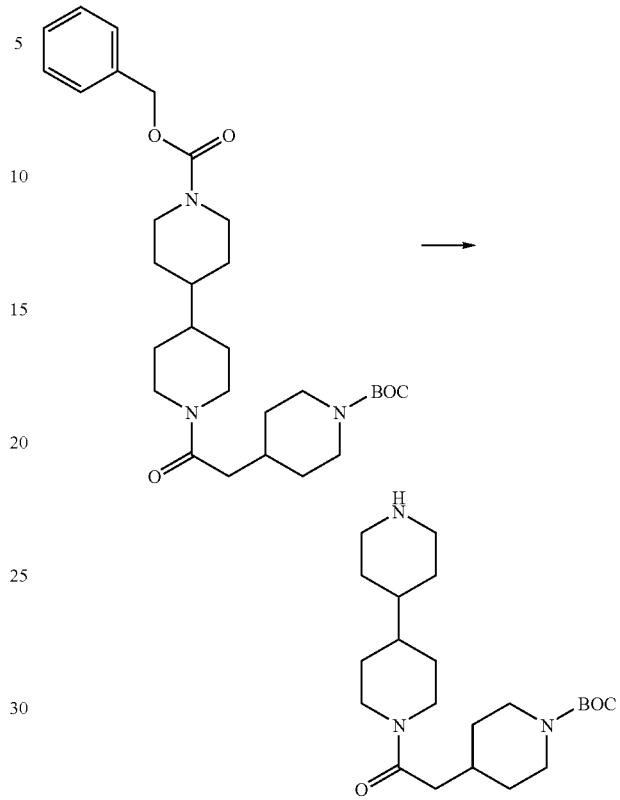

A suspension of the title compound from Preparative Example 23, STEP C (1.18 g, 2.24 mmol) and 10% Pd/C (0.2 g) in MeOH (25 mL) was hydrogenated at room temperature for 2 hr. Catalysts were filtered off through celite. The filtrate was concentrated to give a syrup, which was used without further purification. FABMS: $MH^+$=394.

Preparative Example 24

Step A:

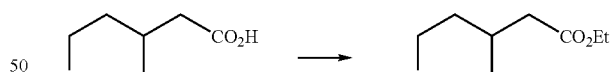

To a solution of piperidine-4-acetic acid (10.0 g, 70.0 mmol) was in EtOH (100 mL) was added concentrated HCl (2.68 mL, 2.2 eq.). The resulting solution was heated at reflux for 12 hours. The reaction mixture was concentrated under reduced pressure and used without further purification (10 g, 84% yield).

Step B:

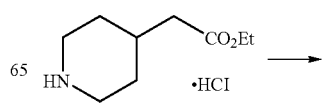

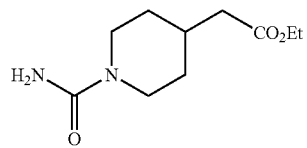

To a solution of the title compound from Preparative Example 24, Step A (2.0 g, 9.6 mmol) in CH$_2$Cl$_2$ (30 mL) at 0° C. was added TMSNCO (6.3 mL, 5.0 eq.) followed by TEA (2.0 mL, 1.5 eq.). The resulting solution was stirred at 0° C. for 3 hours and quenched by the addition water and diluted with saturated NaHCO$_3$. The mixture was extracted with CH$_2$Cl$_2$ and the combined organics dried over Na$_2$SO$_4$, filtered, and concentrated. The crude product was purified by flash chromatography using an 8% (10% NH$_4$OH in MeOH) in CH$_2$Cl$_2$ as eluent (1.2 g, 60% yield). FABMS: MH$^+$=215.

Step C:

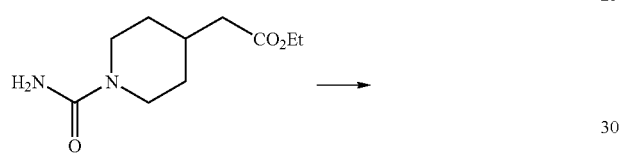

A solution of the title compound from Preparative Example 24, Step B (1.23 g, 5.7 mmol) and LiOH (0.33 g, 2.4 eq.) in CH$_2$Cl$_2$ (29 mL), EtOH (29 mL) and water (14 mL) was heated at reflux 3 hours. The resulting solution was cooled to room temperature, neutralized by the addition of 1N HCl (16.1 mL, 2.98 eq.) and concentrated under reduced pressure. The reaction product was further dried by the azeotropic removal of water with toluene to yield an off-white gum (1.1 g, quantitative yield). FABMS: MH$^+$=187.

Preparative Example 25

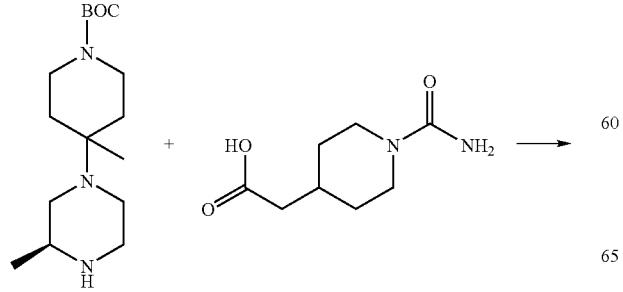

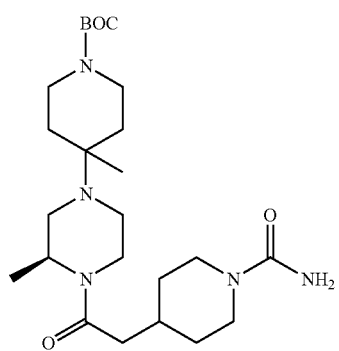

By essentially the same procedure set forth in Preparative Example 23, STEP C, only substituting the title compound from Preparative Example 24 and piperidine-piperidine compound (prepared according to known procedures) gave the title compound.

Preparative Example 26

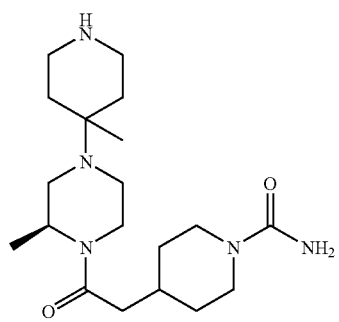

By essentially the same procedure set forth in Preparative Example 23, STEP B only substituting the title compound from Preparative Example 25, gave the title compound. LCMS: MH$^+$=366.

Preparative Example 27

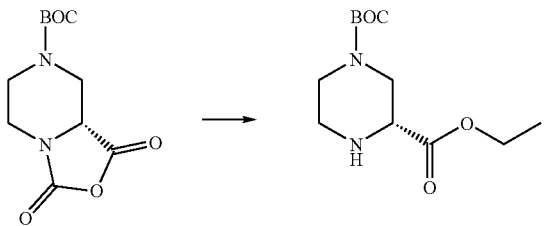

A solution of the piperazine-anhydride compound (prepared according to known procedures, 0.2 g, 0.78 mmol) in EtOH (5 mL) was heated at reflux until the starting material was gone. The resulting solution was cooled to room temperature and concentrated under reduced pressure to yield the desired product.

Preparative Example 28

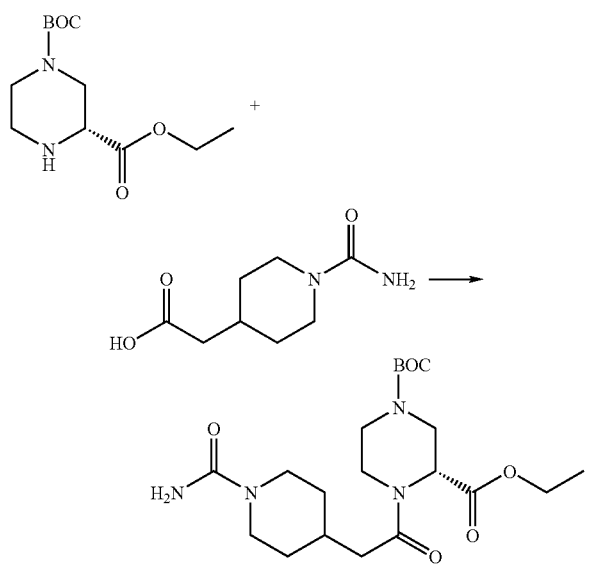

By essentially the same procedure set forth in Preparative Example 23, STEP C, only substituting the title compound from Preparative Example 27, gave the title compound. mp=70-76° C. FABMS: MH$^+$=427.

Preparative Example 29

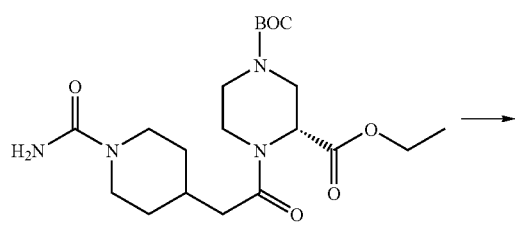

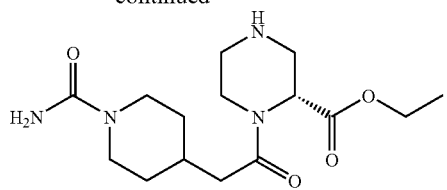

By essentially the same procedure set forth in Preparative Example 23, STEP B, only substituting the title compound from Preparative Example 28, gave the title compound. LCMS: MH$^+$=327.

Preparative Examples 30-37

The synthesis of desired chlorides in Table 5, Column 2 is described in corresponding patents and patent applications (see, for example, U.S. Pat. No. 5,719,148).

TABLE 5

| Prep. Ex. | Chloride | Reference |
|---|---|---|
| 30 | ![structure] | |
| 31 | ![structure] | |
| 32 | ![structure] | |
| 33 | ![structure] | |
| 34 | ![structure] | |
| 35 | ![structure] | |

49

TABLE 5-continued

| Prep. Ex. | Chloride | Reference |
|---|---|---|
| 36 | 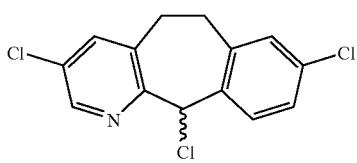 | |
| 37 | 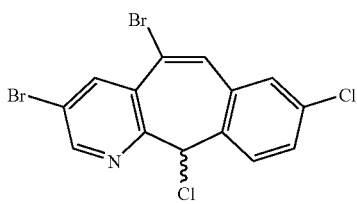 | |

Preparative Example 38

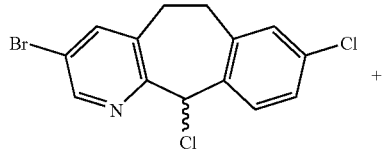

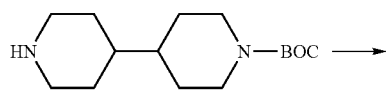

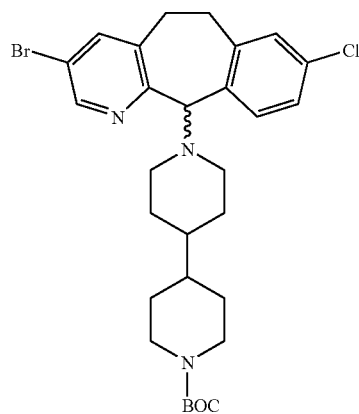

50

To a solution of the title compound from Example 21 (0.47 g, 1.75 mmol, 1.135 eq.) and $Et_3N$ (0.24 mL) in anhydrous $CH_2Cl_2$ (20 mL) was added the freshly prepared compound from Preparative Example 32 (1.54 mmol) in anhydrous $CH_2Cl_2$ (5 mL). The resulting mixture was stirred at r.t. for 16 hrs and the solvent was evaporated under vacuum. The residue was purified by flash chromatography using 5%, 10% and 15% EtOAc in Hexane as eluent to give a white puff solid (0.8 g, 90% yield). FABMS: $MH^+$=574.

Preparative Example 39

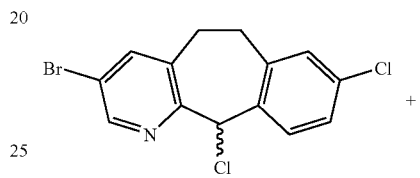

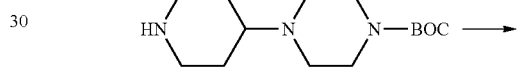

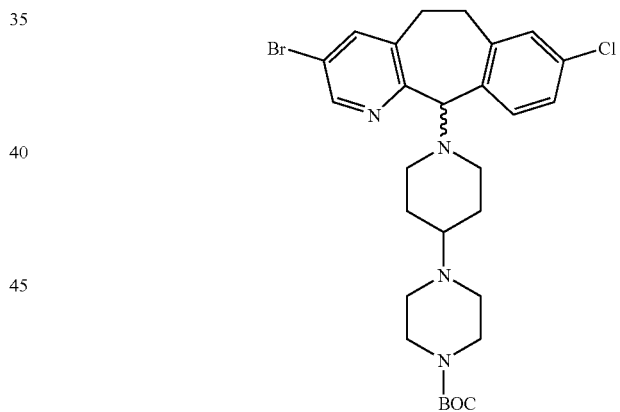

By essentially the same procedure set forth in Preparative Example 38, only substituting the title compound from Preparative Example 22 (0.475 g, 1.76 mmol), using 3% MeOH/$CH_2Cl_2$ as eluent, gave the title compound (0.65 g, 73% yield). FABMS: $MH^+$=575.

Preparative Example 40-46

By essentially the same procedure set forth in Preparative Example 38 or Preparative Example 39, only substituting the chlorides from Table 6, Column 2, the title compounds in Table 6, Column 3 were prepared:

TABLE 6
| Prep. Ex. | Column 2 | Column 3 | DATA |
|---|---|---|---|
| 40 | | | FABMS: MH⁺ = 652 |
| 41 | | | FABMS: MH⁺ = 496. |
| 42 | | | FABMS: MH⁺ = 574. |
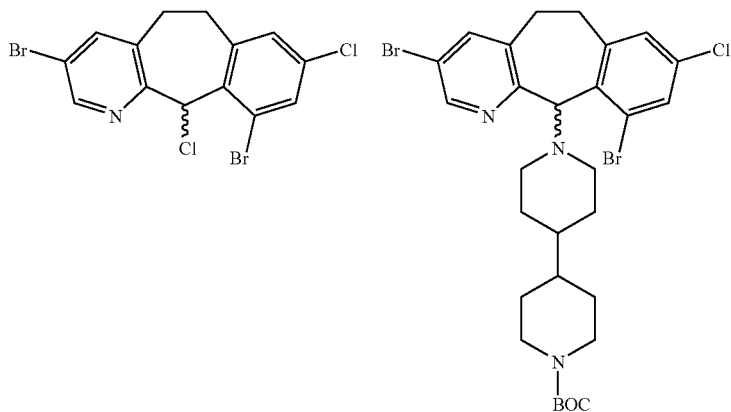
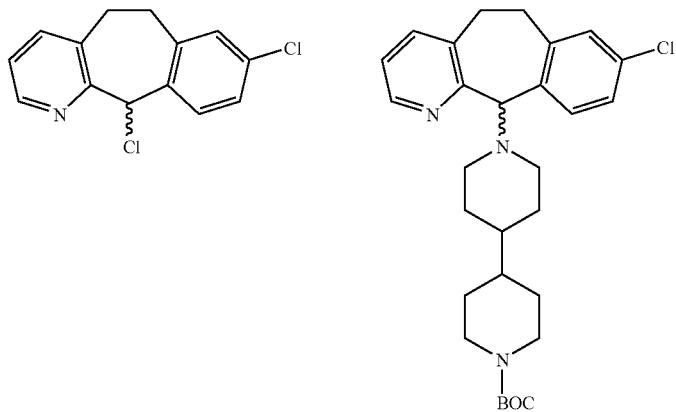
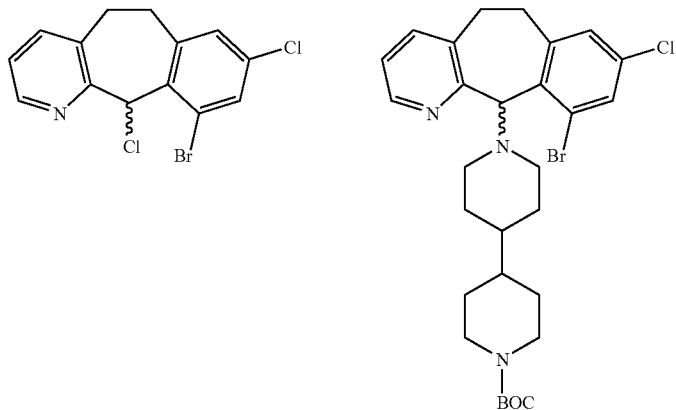

TABLE 6-continued
| Prep. Ex. | Column 2 | Column 3 | DATA |
|---|---|---|---|
| 43 | | | FABMS: MH+ = 652. |
| 44 | | | FABMS: MH+ = 530. |
| 45 | | | FABMS: MH+ = 652. |
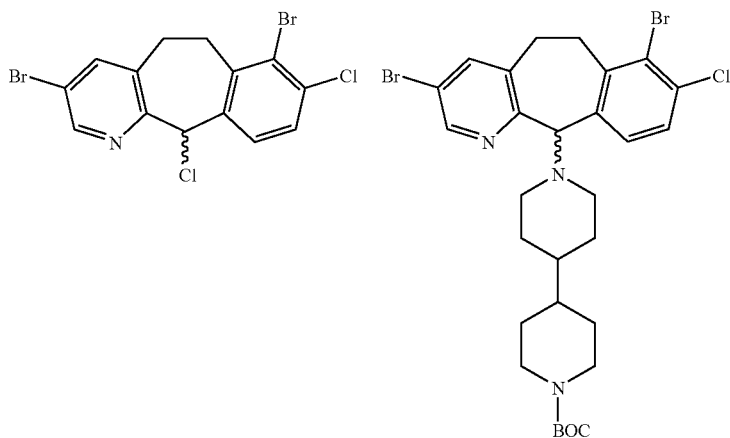
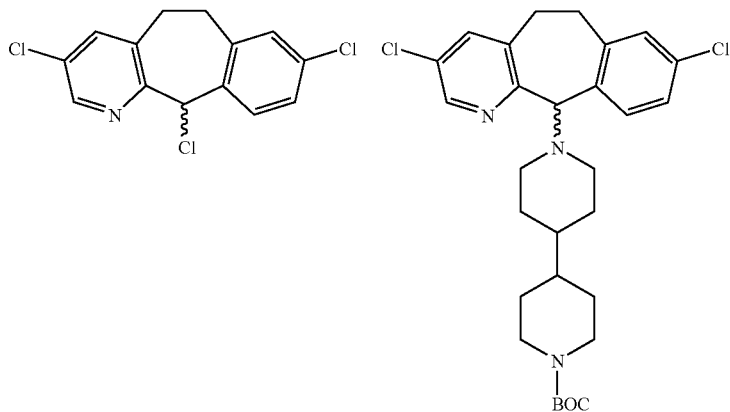
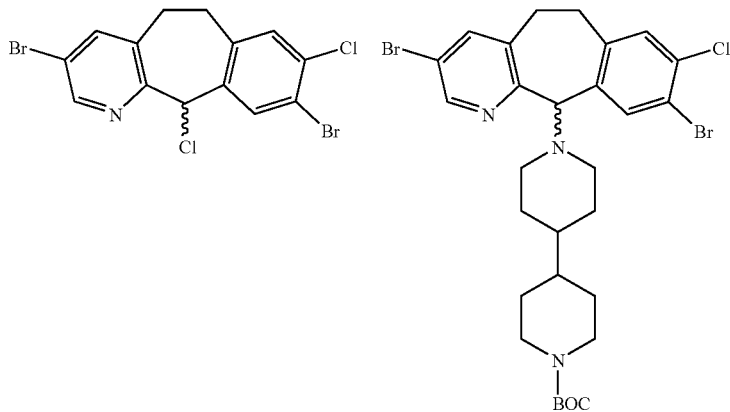

TABLE 6-continued

| Prep. Ex. | Column 2 | Column 3 | DATA |
|---|---|---|---|
| 46 | | | FABMS: MH+ = 606. |

Preparative Example 47

Preparative Example 48

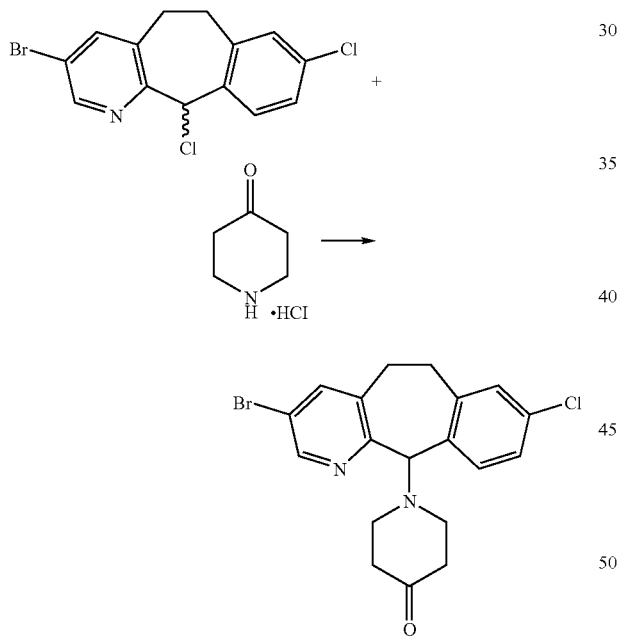

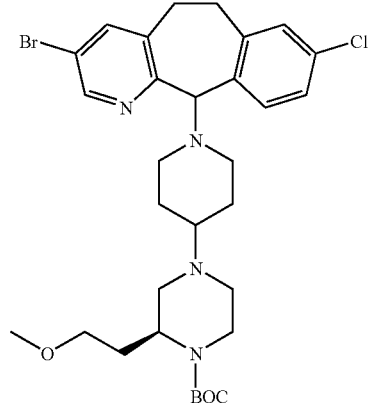

To a solution of 4-piperidone (0.2 g, 1.3 mmol) in DMF (5 mL) was added Et₃N (0.95 mL, 6.5 mmol, 5 eq.) and stirred for 0.5 hr. To the reaction mixture was added the title compound from Preparative Example 30 (0.67 g, 1.95 mmol, 1.5 eq.) and stirred overnight. The reaction was quenched by the addition of saturated NaHCO₃ and extracted with CH₂Cl₂. The combined organics were dried over Na₂SO₄, filtered and concentrated. The crude product was purified by flash chromatography using a 3% EtOAc in CH₂Cl₂ solution as eluent to yield the desired product (0.4 g, 73% yield). FABMS: MH+=405.

To a solution of the title compound from Preparative Example 19 (0.15 g, 0.617 mmol) and the title compound from Preparative Example 47 (0.254 g, 0.629 mmol, 1.02 eq.) in dry CH$_2$Cl$_2$ (5 mL) was added NaBH(OAc)$_3$, acetic acid (0.05 mL) and stirred for 3 days. The reaction was basified by the addition of 50% NaOH and extracted with CH$_2$Cl$_2$. The combined organics were washed with brine, dried over Na$_2$SO$_4$, filtered and concentrated. The crude product was purified by flash chromatography using a 3% MeOH/CH$_2$Cl$_2$ as eluent to yield the white solid (0.163 g, 42% yield). mp=83-87° C. FABMS: MH$^+$=633.

Preparative Examples 49-52

By essentially the same procedure set forth in Preparative Example 8 only substituting the piperazine from Column 2 of Table 7, the title compounds in Column 3, Table 7 were prepared.

TABLE 7

| Prep. Ex. | Column 2 | Column 3 | DATA |
|---|---|---|---|
| 49 | | | FABMS: MH$^+$ = 631. |
| 50 | | | LCMS: MH$^+$ = 517. |

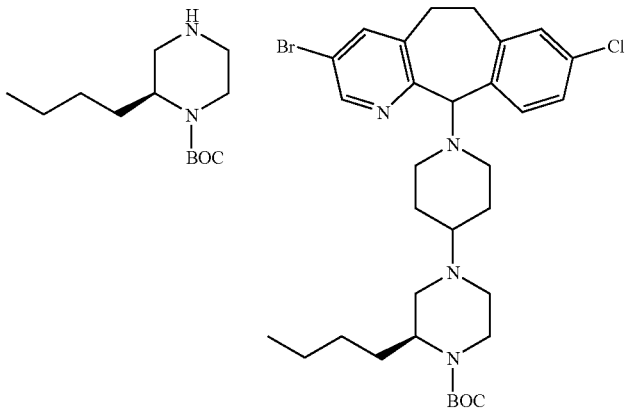

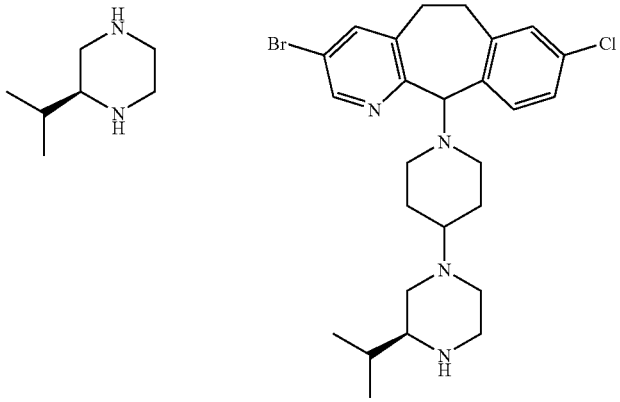

TABLE 7-continued
| Prep. Ex. | Column 2 | Column 3 | DATA |
|---|---|---|---|
| 51 | | | LCMS: MH+ = 531. |
| 52 | | | LCMS: MH+ = 565. |
Preparative Example 53
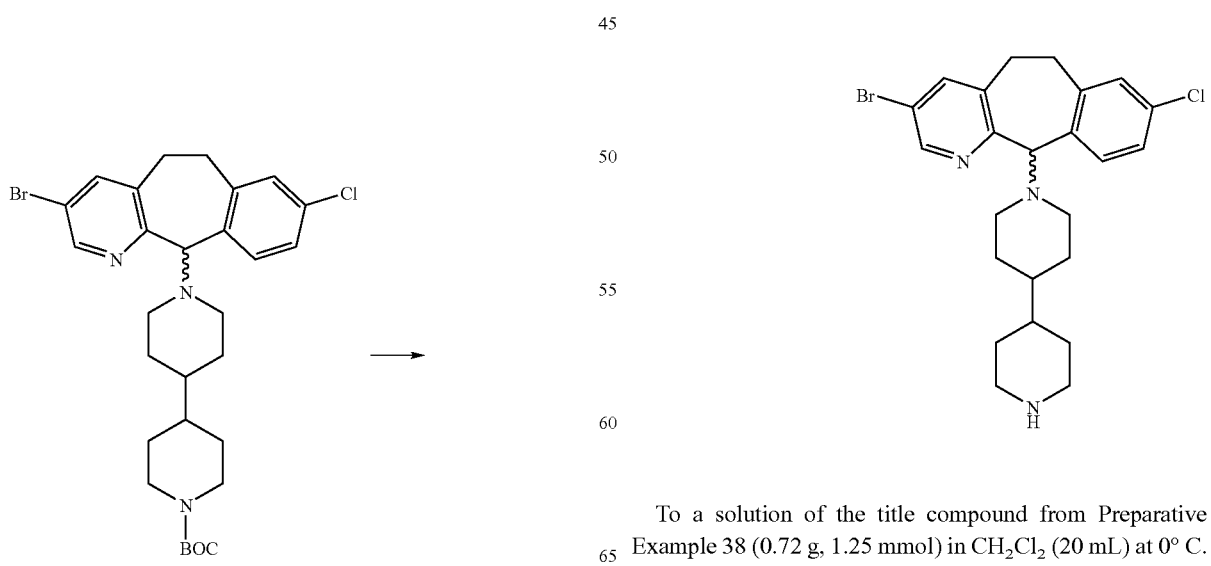
To a solution of the title compound from Preparative Example 38 (0.72 g, 1.25 mmol) in $CH_2Cl_2$ (20 mL) at 0° C. was added dropwise TFA (11 mL). The resulting mixture was stirred at 0-5° C. for 2 hrs, then concentrated under reduced pressure. The residue was dissolved in CH₂Cl₂/H₂O, adjusted PH to 13 by the addition of 1N NaOH, separated, extracted aqueous layer with CH₂Cl₂. The combined organics were dried over Na₂SO₄, filtered and concentrated to give a white solid (0.59 g, 99% yield) which was used without further purification. FABMS: MH$^+$=474.

Preparative Example 54-63

By essentially the same procedure set forth in Preparative Example 53 only substituting the compounds from Table 8, Column 2, the title compounds in Table 8, Column 3 were prepared:

TABLE 8

| Prep. Ex. | Column 2 | Column 3 | DATA |
|---|---|---|---|
| 54 | | | FABMS: MH$^+$ = 475 |
| 55 | | | FABMS: MH$^+$ = 552 |
| 56 | | | FABMS: MH$^+$ = 396. |

TABLE 8-continued
| Prep. Ex. | Column 2 | Column 3 | DATA |
|---|---|---|---|
| 57 | 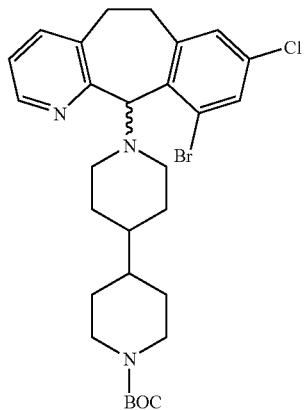 | 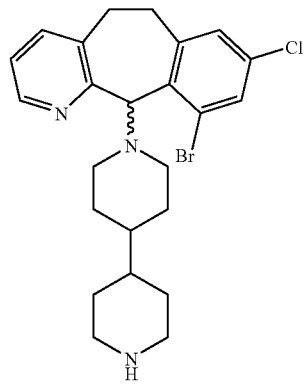 | FABMS: MH+ = 474. |
| 58 | 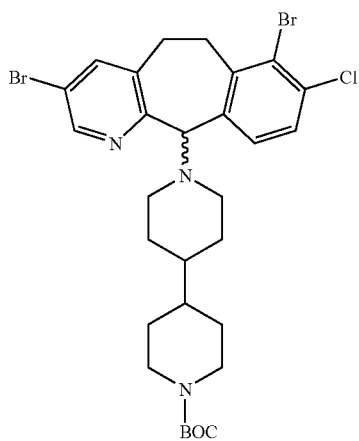 | 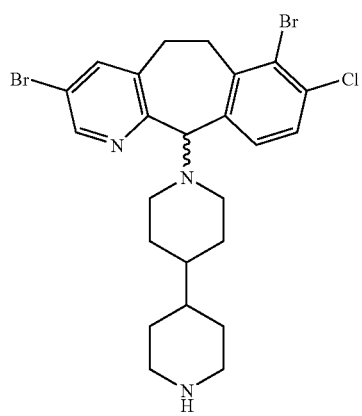 | FABMS: MH+ = 552. |
| 59 | 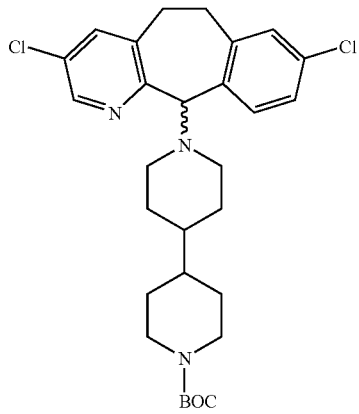 | 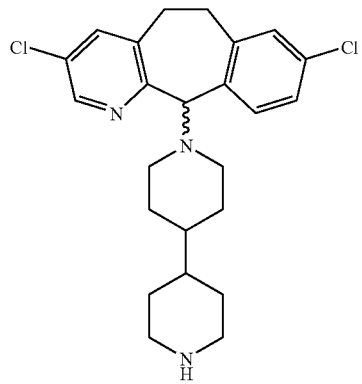 | FABMS: MH+ = 430. |

TABLE 8-continued

| Prep. Ex. | Column 2 | Column 3 | DATA |
|---|---|---|---|
| 60 | | | FABMS: MH$^+$ = 552. |
| 61 | | | FABMS: MH$^+$ = 506. |
| 62 | | | LCMS: MH$^+$ = 533. |

TABLE 8-continued

| Prep. Ex. | Column 2 | Column 3 | DATA |
|---|---|---|---|
| 63 | | | FABMS: MH⁺ = 531. |

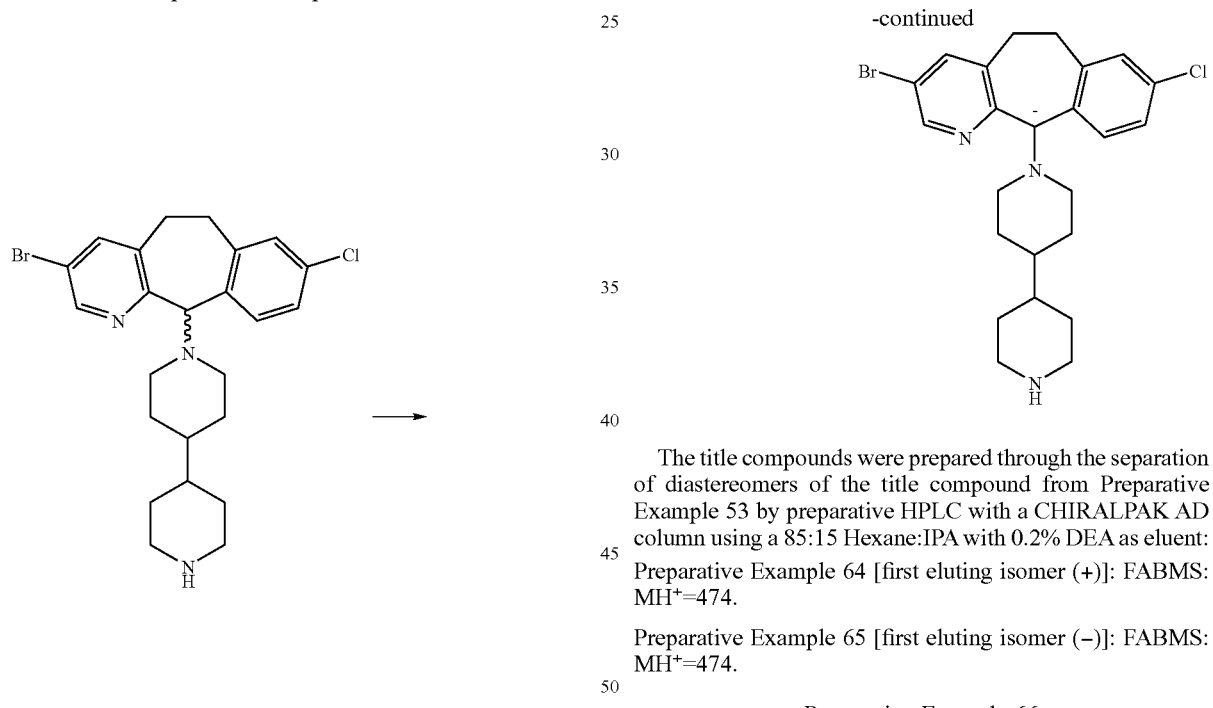

Preparative Examples 64 and 65

The title compounds were prepared through the separation of diastereomers of the title compound from Preparative Example 53 by preparative HPLC with a CHIRALPAK AD column using a 85:15 Hexane:IPA with 0.2% DEA as eluent:

Preparative Example 64 [first eluting isomer (+)]: FABMS: MH$^+$=474.

Preparative Example 65 [first eluting isomer (−)]: FABMS: MH$^+$=474.

Preparative Example 66

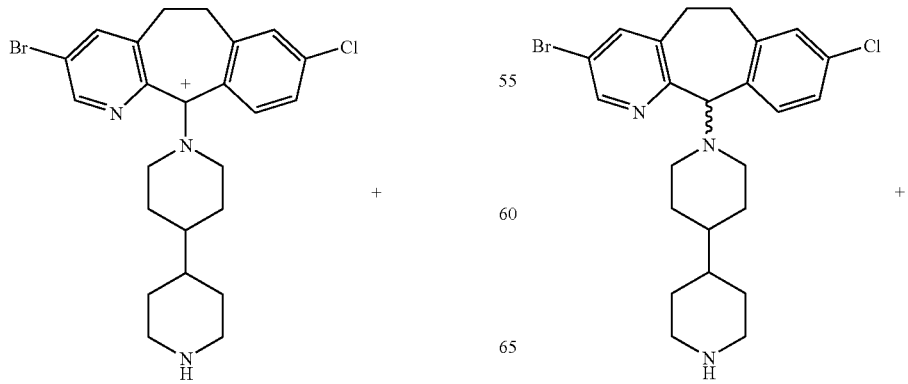

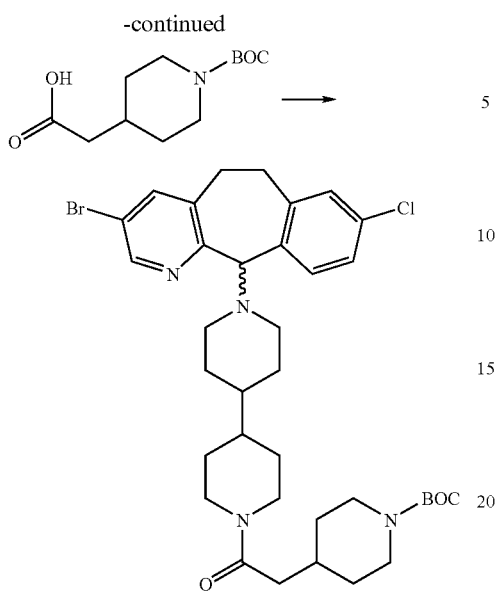

A solution of the title compound from Preparative Example 53 (0.26 g, 0.55 mmol), N-Boc-4-piperidineacid acid (prepared as described in U.S. Pat. No. 5,874,442; 0.2 g, 0.822 mmol), DEC (0.14 g, 0.73 mmol), HOBt (0.096 g, 0.71 mmol), and NMM (0.1 mL, 0.91 mmol) in anhydrous DMF (8.0 mL) was stirred at room temperature for 24 hrs. The reaction was quenched by the addition of 1N NaOH and extracted with $CH_2Cl_2$. The combined organics were dried over $Na_2SO_4$, filtered, and concentrated. The crude product was purified by flash chromatography using a 2% MeOH in $CH_2Cl_2$ solution as eluent to give a yellow puff solid (1.38 g, 99% yield). FABMS: $MH^+$=699.

Preparative Example 67-81

By essentially the same procedure set forth in Preparative Example 66 only substituting the compounds from Table 9, Column 2, the title compounds in Table 9, Column 3 were prepared:

TABLE 9

| Prep. Ex. | Column 2 | Column 3 | DATA |
|---|---|---|---|
| 67 | | | FABMS: $MH^+$ = 699. |
| 68 | | | FABMS: $MH^+$ = 699. |

TABLE 9-continued

| Prep. Ex. | Column 2 | Column 3 | DATA |
|---|---|---|---|
| 69 | | | FABMS: MH+ = 700 |
| 70 | | | FABMS: MH+ = 777. |
| 71 | | | FABMS: MH+ = 621. |

TABLE 9-continued

| Prep. Ex. | Column 2 | Column 3 | DATA |
|---|---|---|---|
| 72 | | | FABMS: MH$^+$ = 699. |
| 73 | | | FABMS: MH$^+$ = 777. |
| 74 | | | FABMS: MH$^+$ = 655. |

TABLE 9-continued

| Prep. Ex. | Column 2 | Column 3 | DATA |
|---|---|---|---|
| 75 | | | FABMS: MH⁺ = 777. |
| 76 | | | LCMH⁺: MH⁺ = 731. |
| 77 | | | LCMS: MH⁺ = 758. |

TABLE 9-continued
| Prep. Ex. | Column 2 | Column 3 | DATA |
|---|---|---|---|
| 78 | 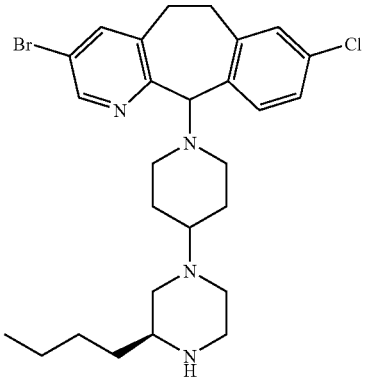 | 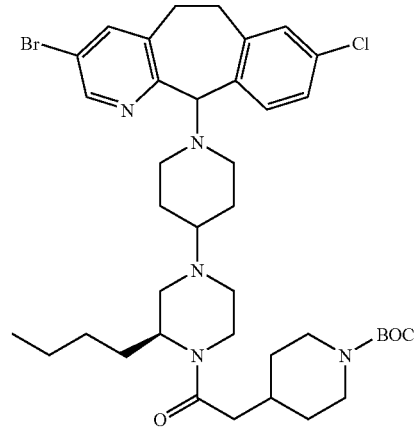 | LCMS: MH+ = 756. |
| 79 | 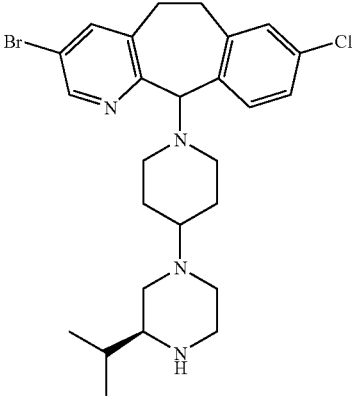 | 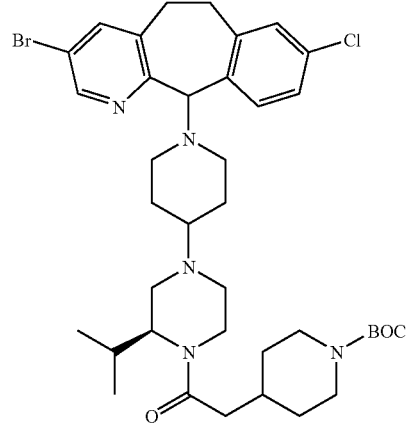 | LCMS: MH+ = 742. |
| 80 | 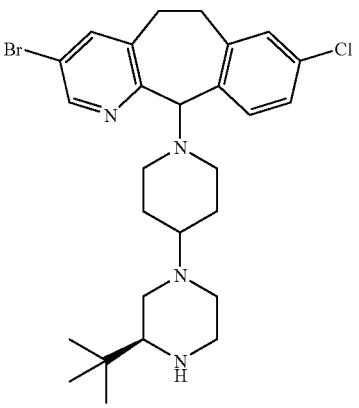 | 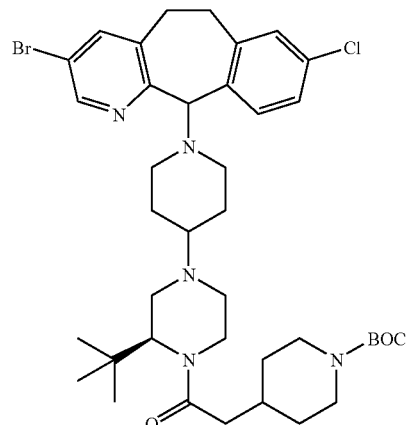 | LCMS: MH+ = 756. |

TABLE 9-continued

| Prep. Ex. | Column 2 | Column 3 | DATA |
|---|---|---|---|
| 81 | | | LCMS: MH+ = 790. |

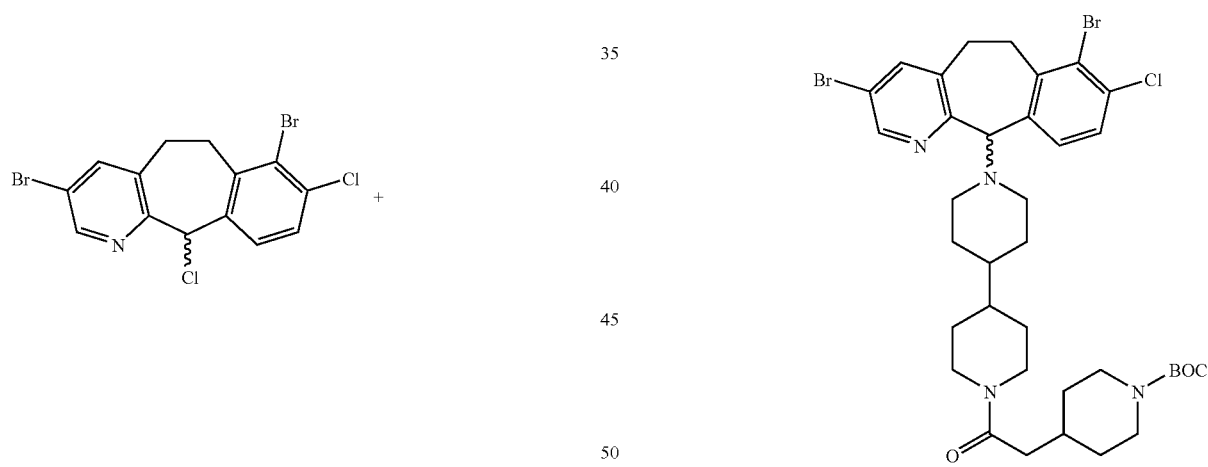

Preparative Example 82

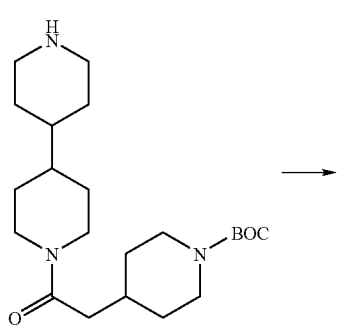

Alternatively, by essentially the same procedure set forth in Preparative Example 38, only substituting the title compound from Preparative Example 36 and the title compound from Preparative Example 25, gave the title compound of this Example (1.09 g, 62% yield). FABMS: MH+=777.

Example 100

By essentially the same procedure set forth in Preparative Example 82 only substituting the compounds from Table 10, Column 2, the compounds from Table 10, Column 3, the title compounds in Table 10, Column 4 were prepared:

TABLE 10

| Ex. | Column 2 | Column 3 | Column 4 | DATA |
|---|---|---|---|---|
| 100 | | | | LCMS: MH+ = 670; m.p. = 108-130° C. |

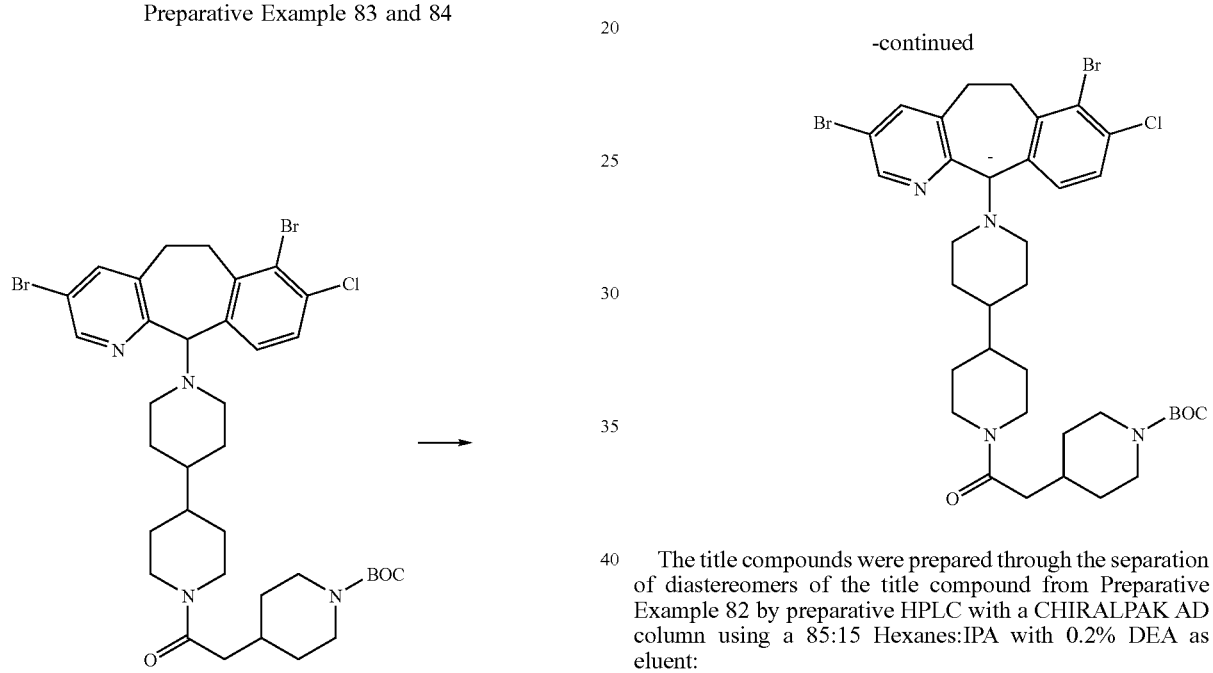

Preparative Example 83 and 84

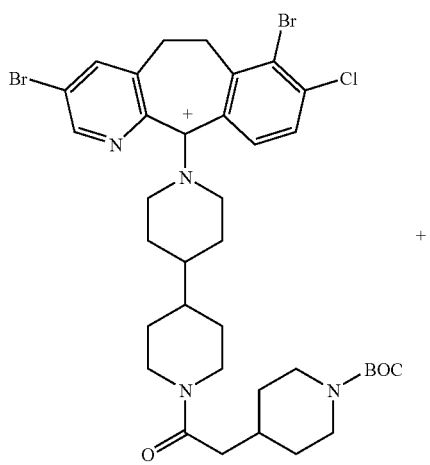

The title compounds were prepared through the separation of diastereomers of the title compound from Preparative Example 82 by preparative HPLC with a CHIRALPAK AD column using a 85:15 Hexanes:IPA with 0.2% DEA as eluent:

Preparative Example 83 [first eluting isomer (+)]: FABMS: MH+=777.

Preparative Example 84 [second eluting isomer (−)]: FABMS: MH+=777.

Preparative Examples 85 and 86

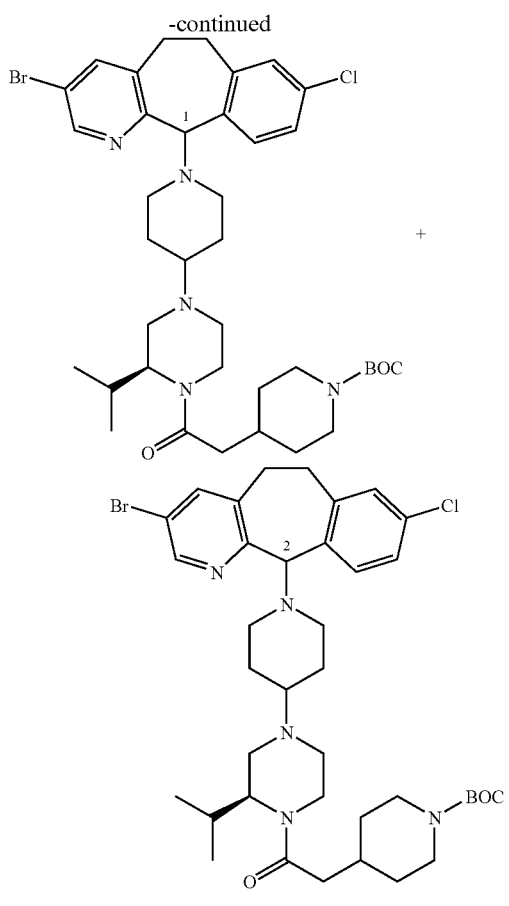

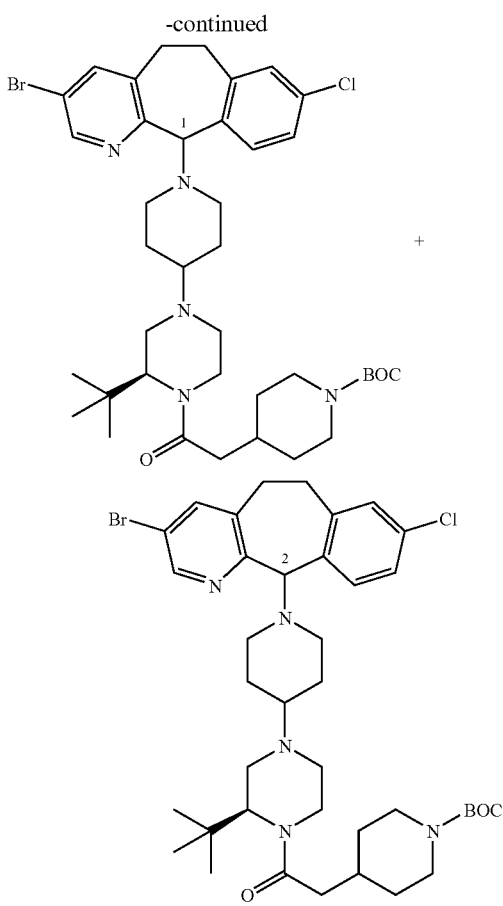

The title compounds were prepared through the separation of diastereomers of the title compound from Preparative Example 79 by preparative HPLC with a CHIRALPAK AD column using a 85:15 Hexane:IPA with 0.2% DEA as eluent:

Preparative Example 85 (first eluting isomer): LCMH$^+$: MH$^+$=742.

Preparative Example 86 (second eluting isomer): LCMH$^+$: MH$^+$=742.

Preparative Example 87 and 88

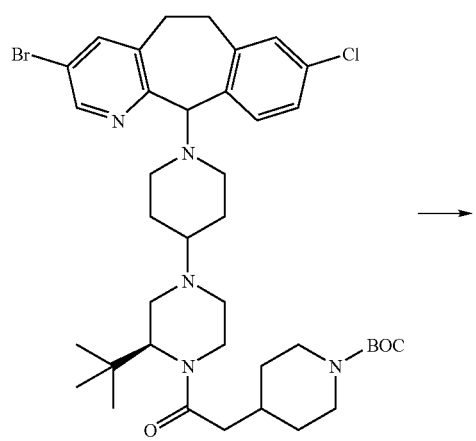

The title compounds were prepared through the separation of diastereomers of the title compound from Preparative Example 80 by preparative HPLC with a CHIRALPAK AD column using a 85:15 Hexane:IPA with 0.2% DEA as eluent:

Preparative Example 87 (first eluting isomer): LCMH$^+$: MH$^+$=756.

Preparative Example 88 (second eluting isomer): LCMH$^+$: MH$^+$=756.

Preparative Example 89

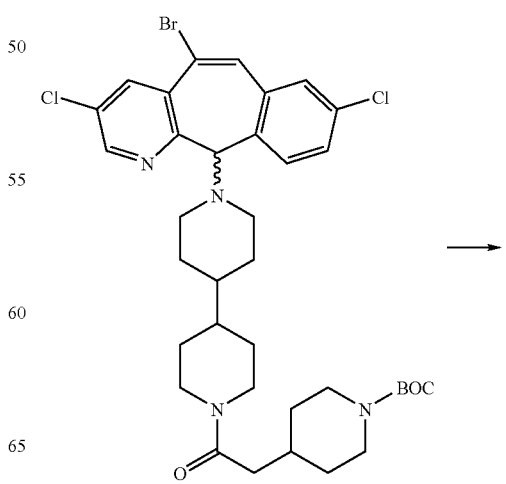

85
-continued

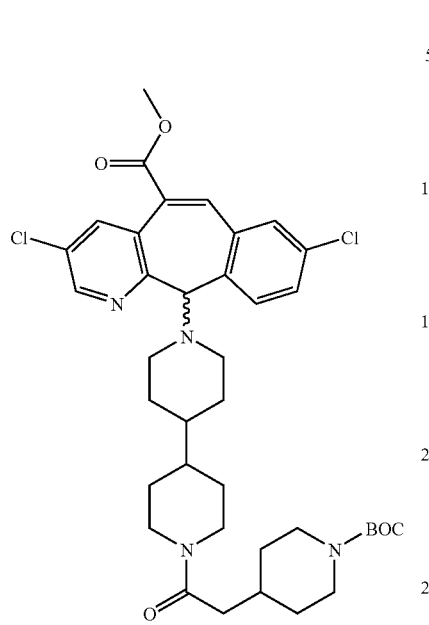

To a solution of the title compound from Preparative Example 76 (0.261 g, 0.36 mmol) in toluene (15 mL) and MeOH (5 mL) was added PPh$_3$ (0.037 g, 0.14 mmol), DBU (0.061 g, 0.40 mmol) and PdCl$_2$ (0.005 g, 0.028 mmol). The resulting mixture was transferred to a CO reactor and heated to 80° C. at 100 psi of CO for 3.5 hrs. The reaction was cooled to r.t., stirred at r.t. for 2 days and concentrated under reduced pressure. The residue was dissolved in 150 mL of EtOAc, washed with H$_2$O, dried over Na$_2$SO$_4$, filtered and concentrated. The crude product was purified by flash chromatography using a 30% EtOAc in CH$_2$Cl$_2$ solution as eluent to give the desired product.

86

Preparative Example 90

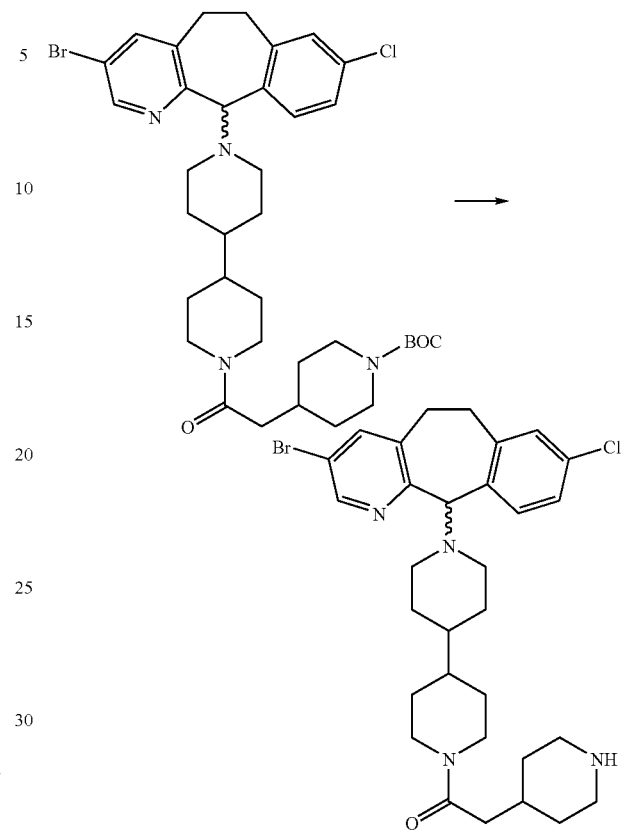

By essentially the same procedure set forth in Preparative Example 23, STEP B, only substituting the title compound from Preparative Example 68 (0.46 g, 0.66 mmol) gave the title compound (0.39 g, 99% yield). FABMS: MH$^+$=599.

Preparative Example 91-112

By essentially the same procedure set forth in Preparative Example 90 only substituting the BOC-compounds from Table 11, Column 2, the title compounds in Table 11, Column 3 were prepared:

TABLE 11

| Prep. Ex. | Column 2 | Column 3 | DATA |
|---|---|---|---|
| 91 | ![structure with BOC] | ![structure with NH] | FABMS: MH$^+$ = 599. |

TABLE 11-continued

| Prep. Ex. | Column 2 | Column 3 | DATA |
|---|---|---|---|
| 92 | | | FABMS: MH⁺ = 599. |
| 93 | | | FABMS: MH⁺ = 600. |
| 94 | | | FABMS: MH⁺ = 677. |

TABLE 11-continued
| Prep. Ex. | Column 2 | Column 3 | DATA |
|---|---|---|---|
| 95 | 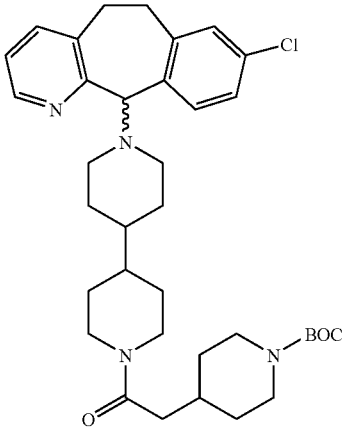 | | FABMS: MH+ = 521. |
| 96 | 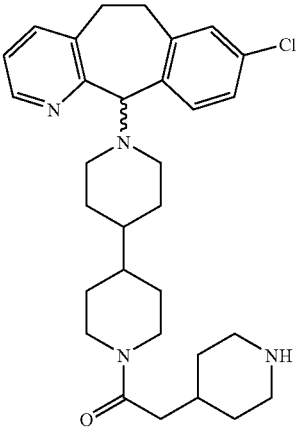 | | FABMS: MH+ = 599. |
| 97 | 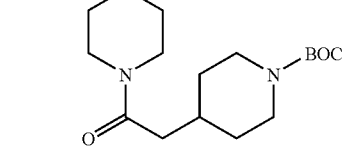 | | FABMS: MH+ = 677. |

TABLE 11-continued

| Prep. Ex. | Column 2 | Column 3 | DATA |
|---|---|---|---|
| 98 | | | FABMS: MH⁺ = 677. |
| 99 | | | FABMS: MH⁺ = 677. |
| 100 | | | FABMS: MH⁺ = 555. |

TABLE 11-continued

| Prep. Ex. | Column 2 | Column 3 | DATA |
|---|---|---|---|
| 101 | | | FABMS: MH+ = 677. |
| 102 | | | LCMH+ MH+ = 611. |
| 103 | | | LCMH+ MH+ = 597. |

TABLE 11-continued
| Prep. Ex. | Column 2 | Column 3 | DATA |
|---|---|---|---|
| 104 | | | LCMH+ MH+ = 658. |
| 105 | | | LCMH+ MH+ = 656. |
| 106 | | | LCMH+ MH+ = 642. |
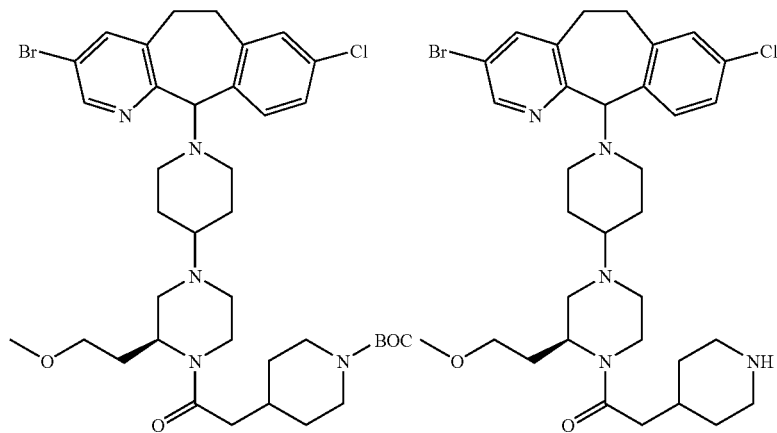
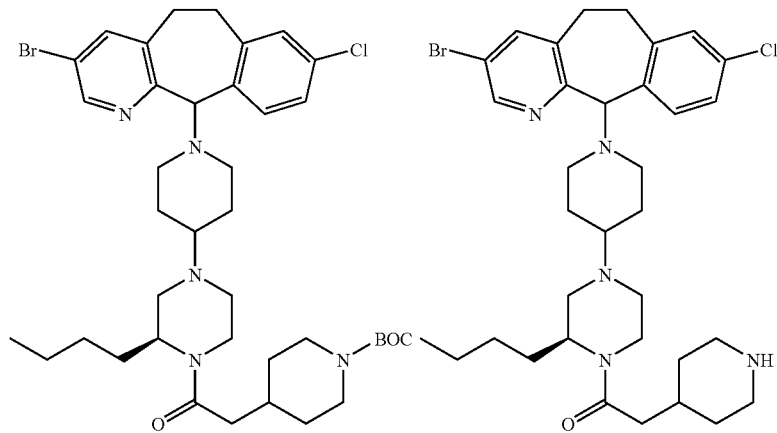
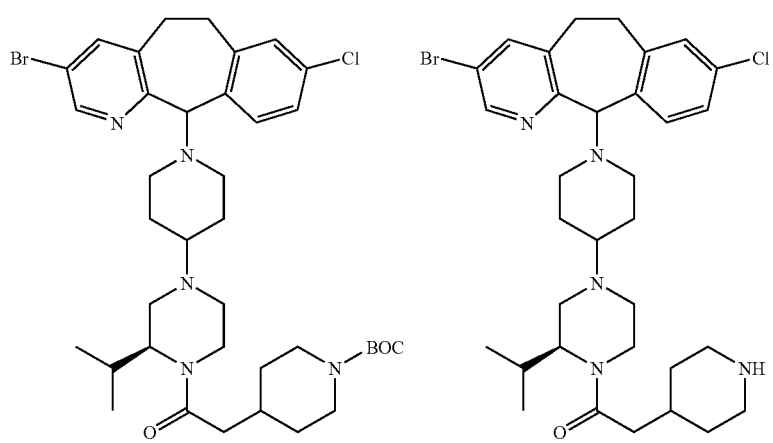

TABLE 11-continued
| Prep. Ex. | Column 2 | Column 3 | DATA |
|---|---|---|---|
| 107 | | | LCMH+ MH+ = 656. |
| 108 | | | LCMH+ MH+ = 642. |
| 109 | | | LCMH+ MH+ = 642. |
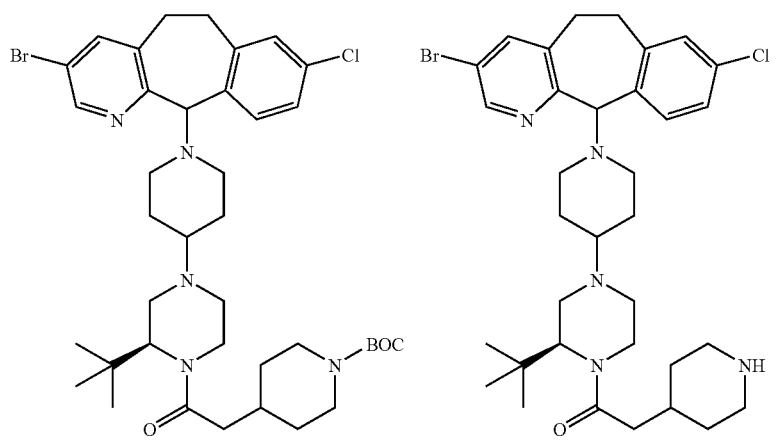
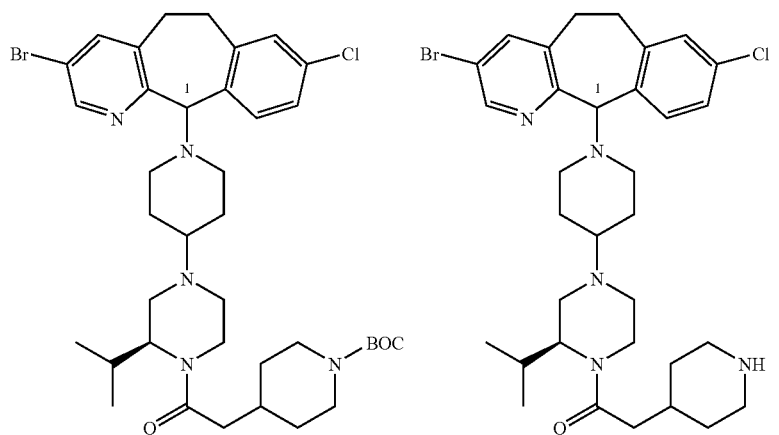
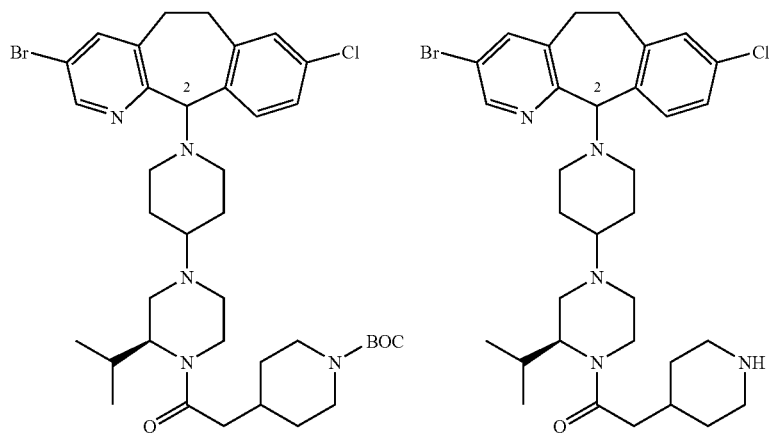

TABLE 11-continued
| Prep. Ex. | Column 2 | Column 3 | DATA |
|---|---|---|---|
| 110 | | | LCMH+ MH+ = 656. |
| 111 | | | LCMH+ MH+ = 656. |
| 112 | | | LCMH+ = 690 |
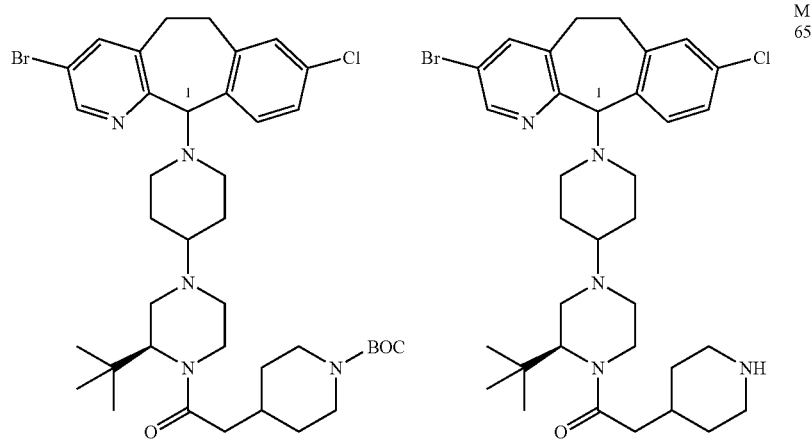
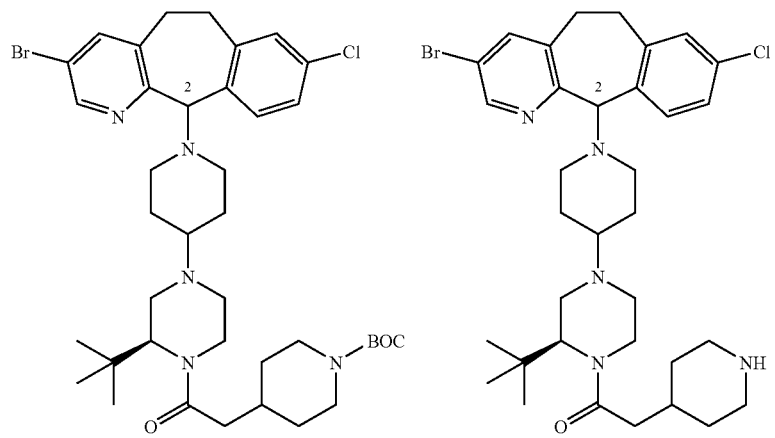
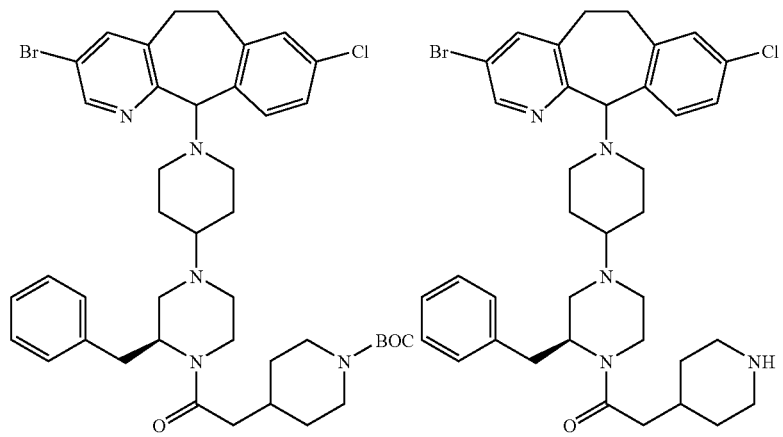

Example 200

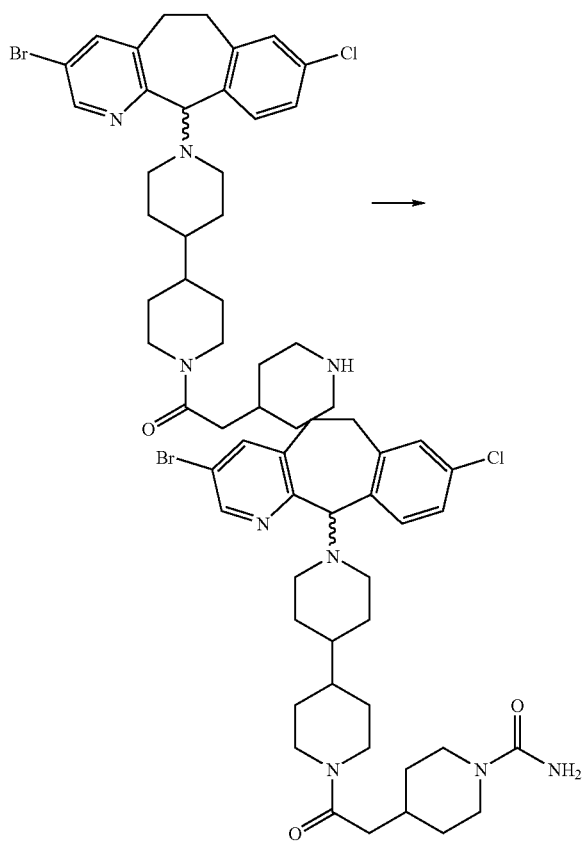

To a solution of the title compound from Preparative Example 90 (0.14 g, 0.233 mmol) in CH$_2$Cl$_2$ (4 mL) at r.t. under N$_2$ was added 85% TMSNCO (0.25 mL, 1.89 mmol). The reaction mixture was stirred at r.t. overnight. The reaction was quenched by the addition of saturated NaHCO$_3$ and extracted with CH$_2$Cl$_2$. The combined organics were dried over Na$_2$SO$_4$, filtered and concentrated. The crude product was purified by flash chromatography using a 5% (10% NH$_4$OH in MeOH) in CH$_2$Cl$_2$ solution as eluent to yield the white amorphous powder (0.105 g, 70% yield). FABMS: MH$^+$=642.

Examples 300-2400

By essentially the same procedure set forth in Example 200 only substituting the compounds from Table 12, Column 2, the title compounds in Table 12, Column 3 were prepared:

TABLE 12

| Prep. Ex. | Column 2 | Column 3 | DATA |
|---|---|---|---|
| 300 | | | FABMS: MH$^+$ = 642. |

TABLE 12-continued
| Prep. Ex. | Column 2 | Column 3 | DATA |
|---|---|---|---|
| 400 | 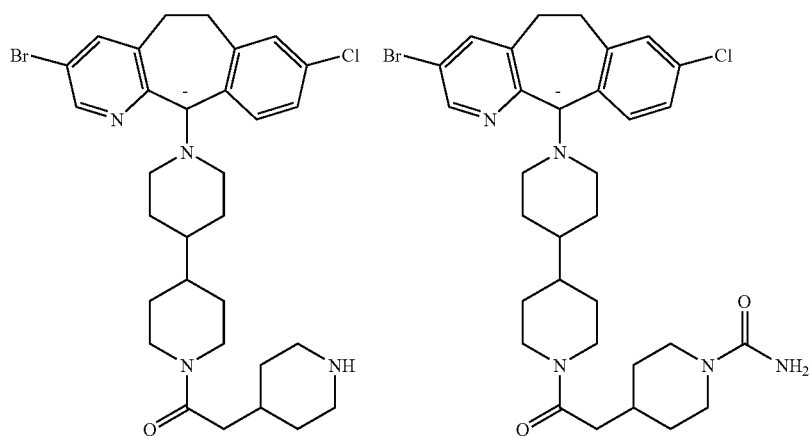 | | FABMS: MH+ = 642. |
| 500 | 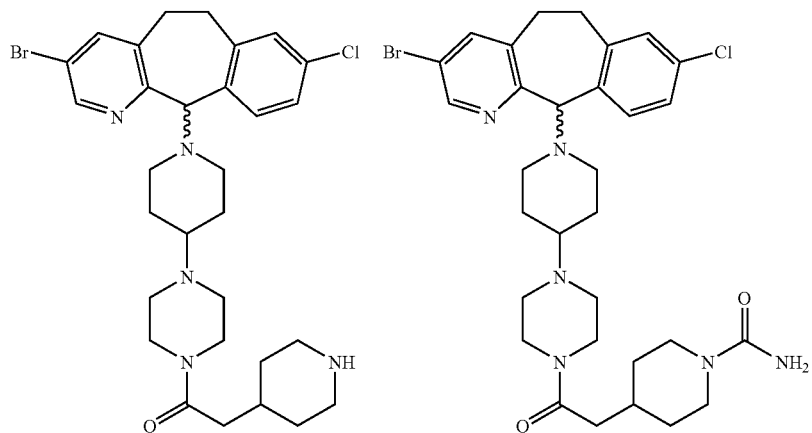 | | FABMS: MH+ = 643. |
| 600 | 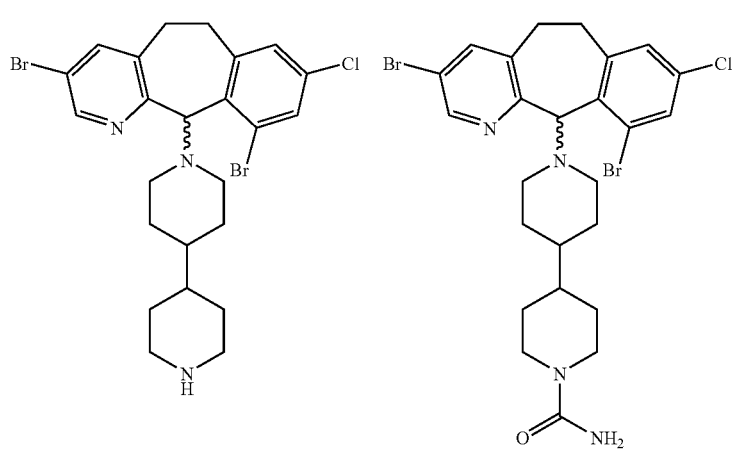 | | FABMS: MH+ = 595. |

TABLE 12-continued
| Prep. Ex. | Column 2 | Column 3 | DATA |
|---|---|---|---|
| 700 | | | FABMS: MH+ = 720. |
| 800 | | | FABMS: MH+ = 564. |
| 900 | | | FABMS: MH+ = 642; mp =. |
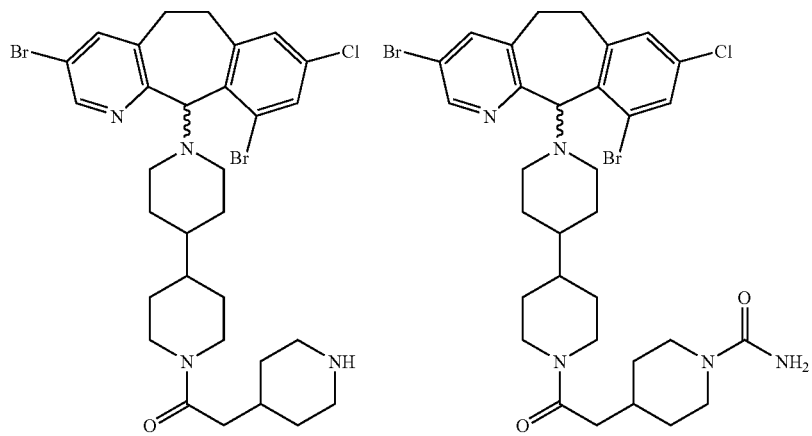
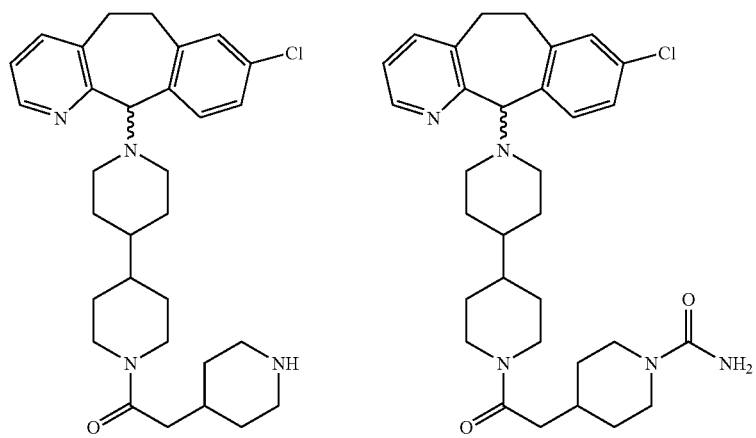
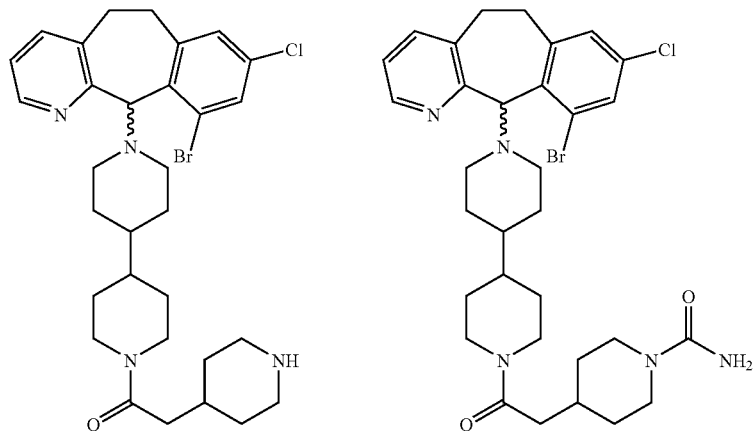

TABLE 12-continued
| Prep. Ex. | Column 2 | Column 3 | DATA |
|---|---|---|---|
| 1000 | | | FABMS: MH+ = 720. |
| 1100 | | | FABMS: MH+ = 720. |
| 1200 | | | FABMS: MH+ = 720. |
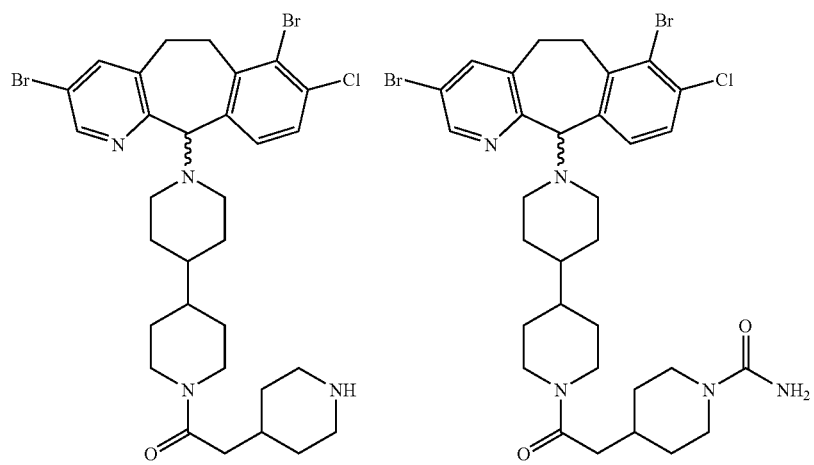
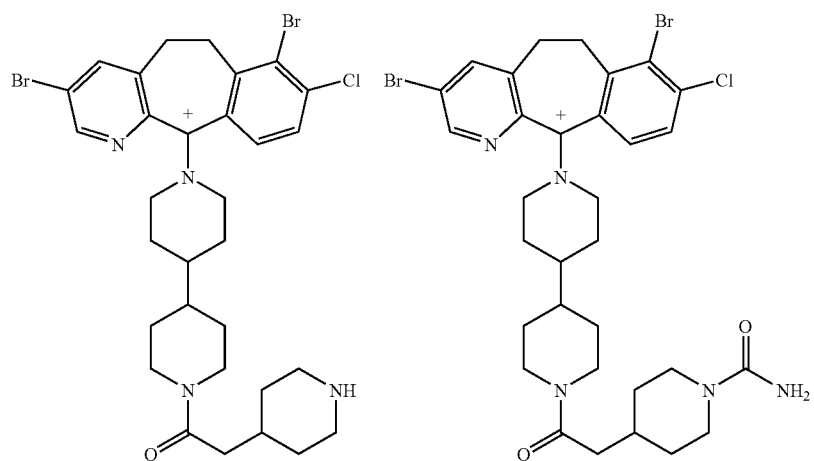
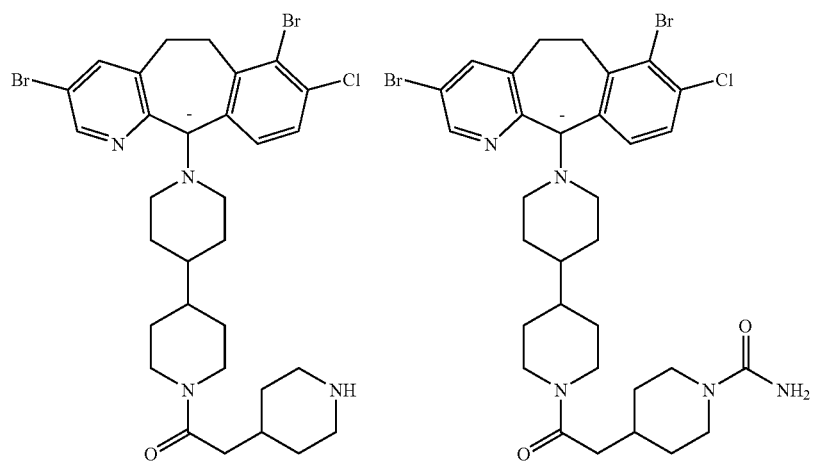

TABLE 12-continued
| Prep. Ex. | Column 2 | Column 3 | DATA |
|---|---|---|---|
| 1300 | 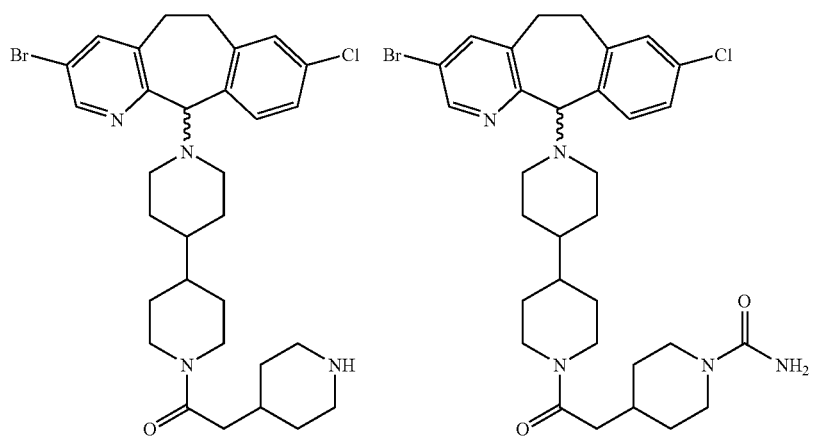 | | FABMS: MH+ = 598; m.p. = 131-140° C. |
| 1400 | 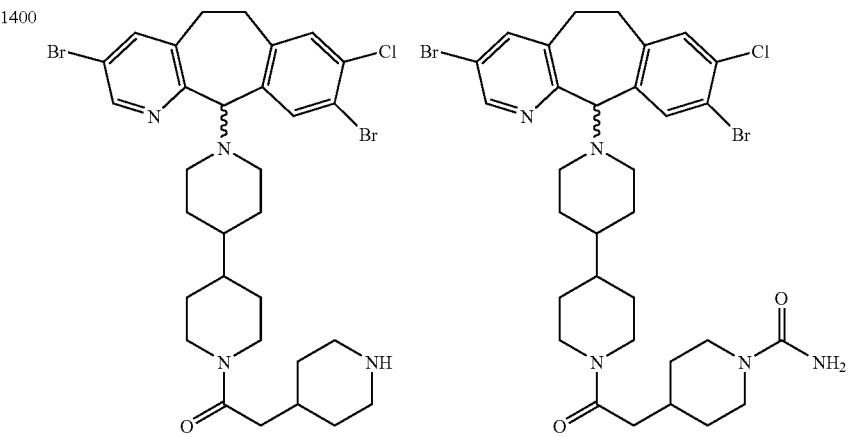 | | FABMS: MH+ = 700; |
| 1500 | 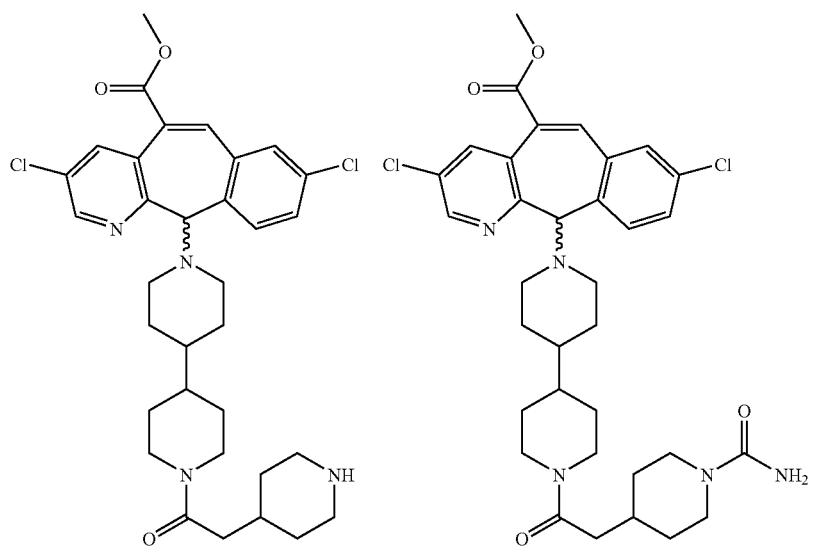 | | LCMS: MH+ = 654; m.p. = 136.8-139.2° C. |

TABLE 12-continued
| Prep. Ex. | Column 2 | Column 3 | DATA |
|---|---|---|---|
| 1600 | | | LCMS: MH+ = 701. m.p. = 93-114° C. |
| 1700 | | | LCMS: MH+ = 699; m.p. = 97.2-97.9° C. |
| 1800 | | | LCMS: MH+ = 685; m.p. = 93-120° C. |
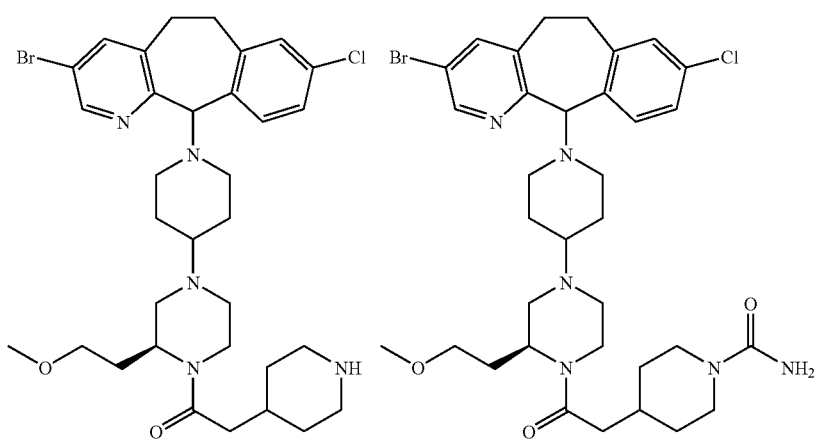
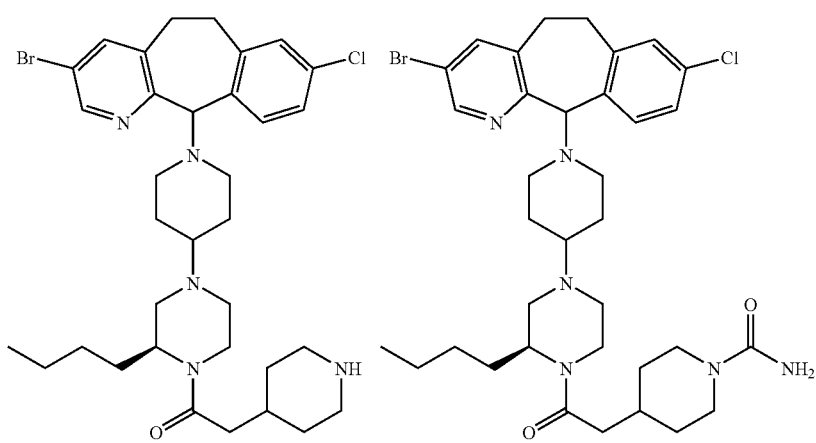
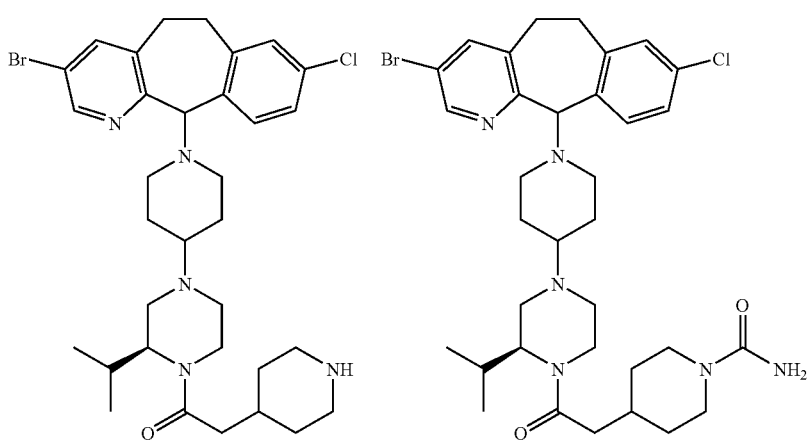

TABLE 12-continued
| Prep. Ex. | Column 2 | Column 3 | DATA |
|---|---|---|---|
| 1900 | | | LCMS: MH+ = 699; m.p. = 59-94° C. |
| 2000 | | | LCMS: MH+ = 685; m.p. = 115-126° C. |
| 2100 | | | LCMS: MH+ = 685; m.p. = 84-110° C. |
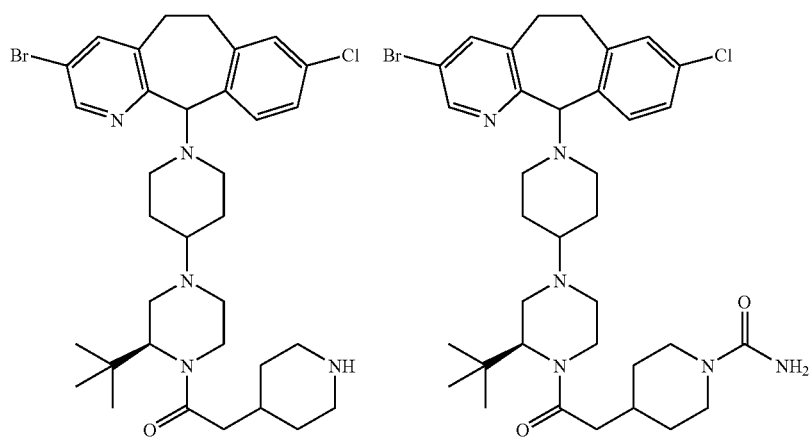
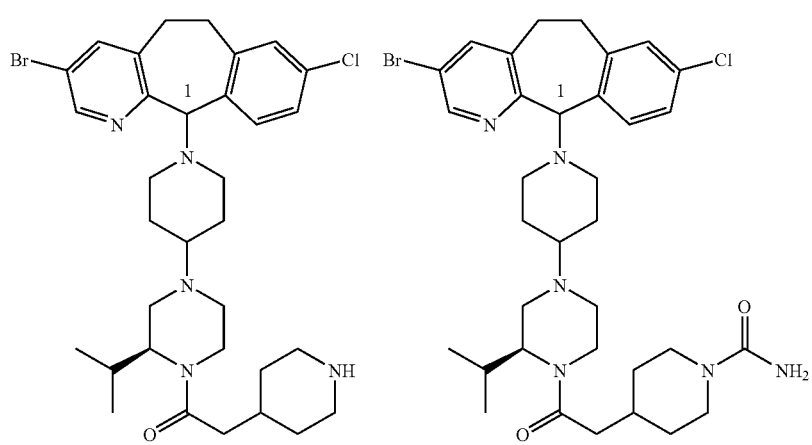
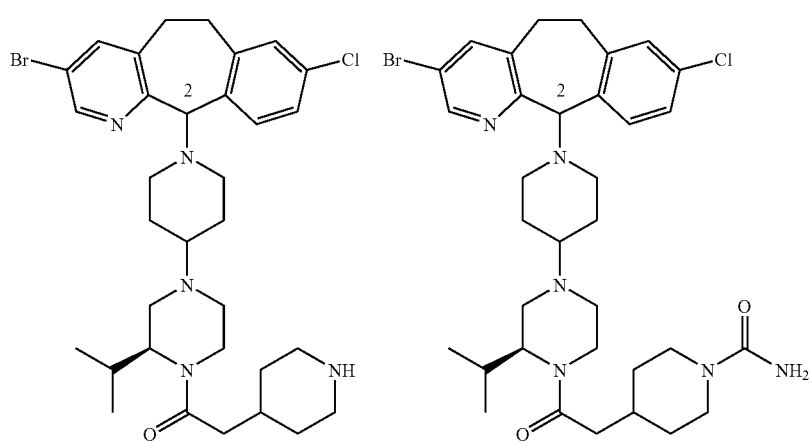

TABLE 12-continued

| Prep. Ex. | Column 2 | Column 3 | DATA |
|---|---|---|---|
| 2200 | (structure with Br, Cl, isomer 1, tert-butyl piperazine, piperidine-NH) | (structure with Br, Cl, isomer 1, tert-butyl piperazine, piperidine-NH-C(O)NH₂) | LCMS: MH⁺ = 699; m.p. = 120-124° C. |
| 2300 | (structure with Br, Cl, isomer 2, tert-butyl piperazine, piperidine-NH) | (structure with Br, Cl, isomer 2, tert-butyl piperazine, piperidine-NH-C(O)NH₂) | LCMS: MH⁺ = 699; m.p. = 106.4-111° C. |
| 2400 | (structure with Br, Cl, benzyl piperazine, piperidine-NH) | (structure with Br, Cl, benzyl piperazine, piperidine-NH-C(O)NH₂) | LCMS: MH⁺ = 733; m.p. = 98-107° C. |

Example 2500

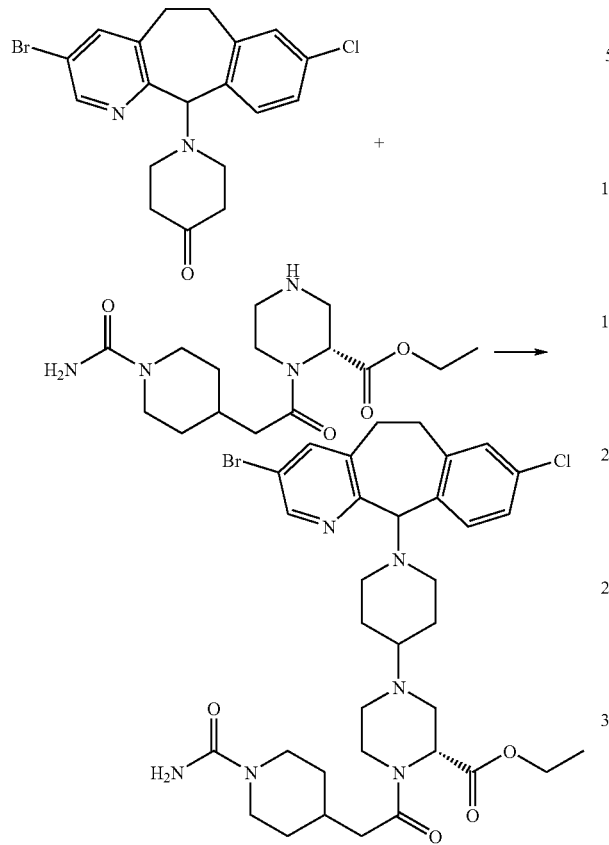

By essentially the same procedure set forth in Preparative Example 48 only substituting the piperazine from the title compound of Preparative Example 29, gave the desired product. m.p.=91-127° C.; LCMS: MH+=715.

Example 2600

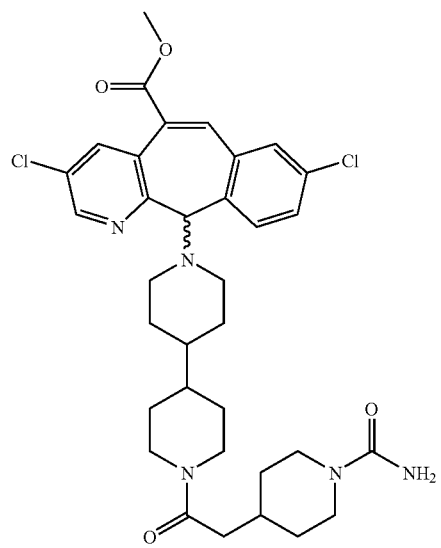

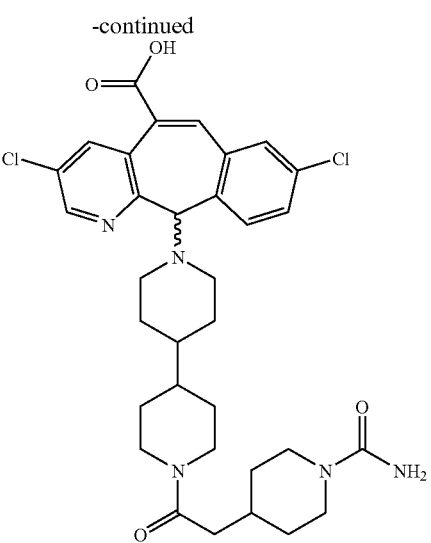

To a solution of the title compound from Example 1500 (0.05 g, 0.08 mmol) in EtOH (1 mL) and H₂O (1 mL) was added LiOH2H₂O and stirred at r.t. overnight. A few drops of 1 M HCl was added to the reaction until it was slightly acidic. The reaction was concentrated and purified by flash chromatography using a 50% MeOH/0.1% HOAc/H₂O as eluent to yield solid (0.042 g, 83% yield). m.p.=131.9-134.8° C. FABMS: MH+=640.

Example 2700

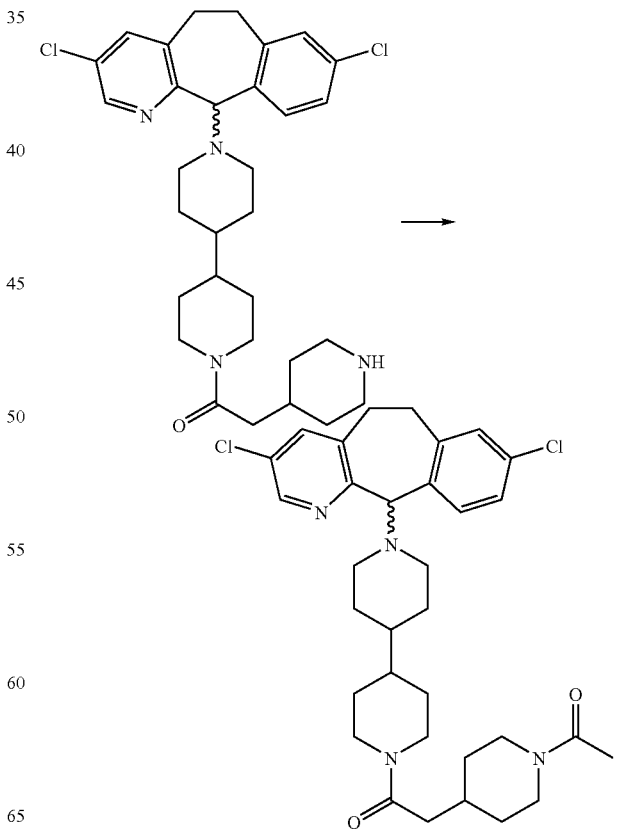

To a solution of the title compound from Preparative Example 100 (0.096 g, 0.153 mmol) in CH$_2$Cl$_2$ (5 mL) at 0° C. was added TEA (0.039 mL, 5 eq.) and AcCl (0.016 mL, 1.2 eq.). The reaction mixture was stirred at r.t. for 2 hrs. The reaction was quenched by the addition of saturated NaHCO$_3$ and extracted with CH$_2$Cl$_2$. The combined organics were dried over Na$_2$SO$_4$, filtered and concentrated. The crude product was purified by flash chromatography using a 7% MeOH in CH$_2$Cl$_2$ solution as eluent to yield a white solid (0.061 g, 66% yield). m.p.=94-101° C.; FABMS: MH$^+$=597.

Examples 2800-3400

By essentially the same procedure set forth in Example only substituting the compound from Table 13, Column, the title compounds shown in Table 13, column 3 were prepared:

TABLE 13

| Prep. Ex. | Column 2 | Column 3 | DATA |
|---|---|---|---|
| 2800 | | | LCMS: MH$^+$ = 516; m.p. = 92-97° C. |
| 2900 | | | LCMS: MH$^+$ = 698; m.p. = 122.3-123.5° C. |
| 3000 | | | LCMS: MH$^+$ = 684; m.p. = 90-104° C. |

TABLE 13-continued

| Prep. Ex. | Column 2 | Column 3 | DATA |
|---|---|---|---|
| 3100 | | | LCMS: MH⁺ = 698; m.p. = 75-87° C. |
| 3200 | | | LCMS: MH⁺ = 698; m.p. = 113-123° C. |
| 3300 | | | LCMS: MH⁺ = 698; m.p. = 120-130° C. |

TABLE 13-continued

| Prep. Ex. | Column 2 | Column 3 | DATA |
|---|---|---|---|
| 3400 | (structure) | (structure) | LCMS: MH+ = 732; m.p. = 115-123° C. |

Examples 3500 and 3600

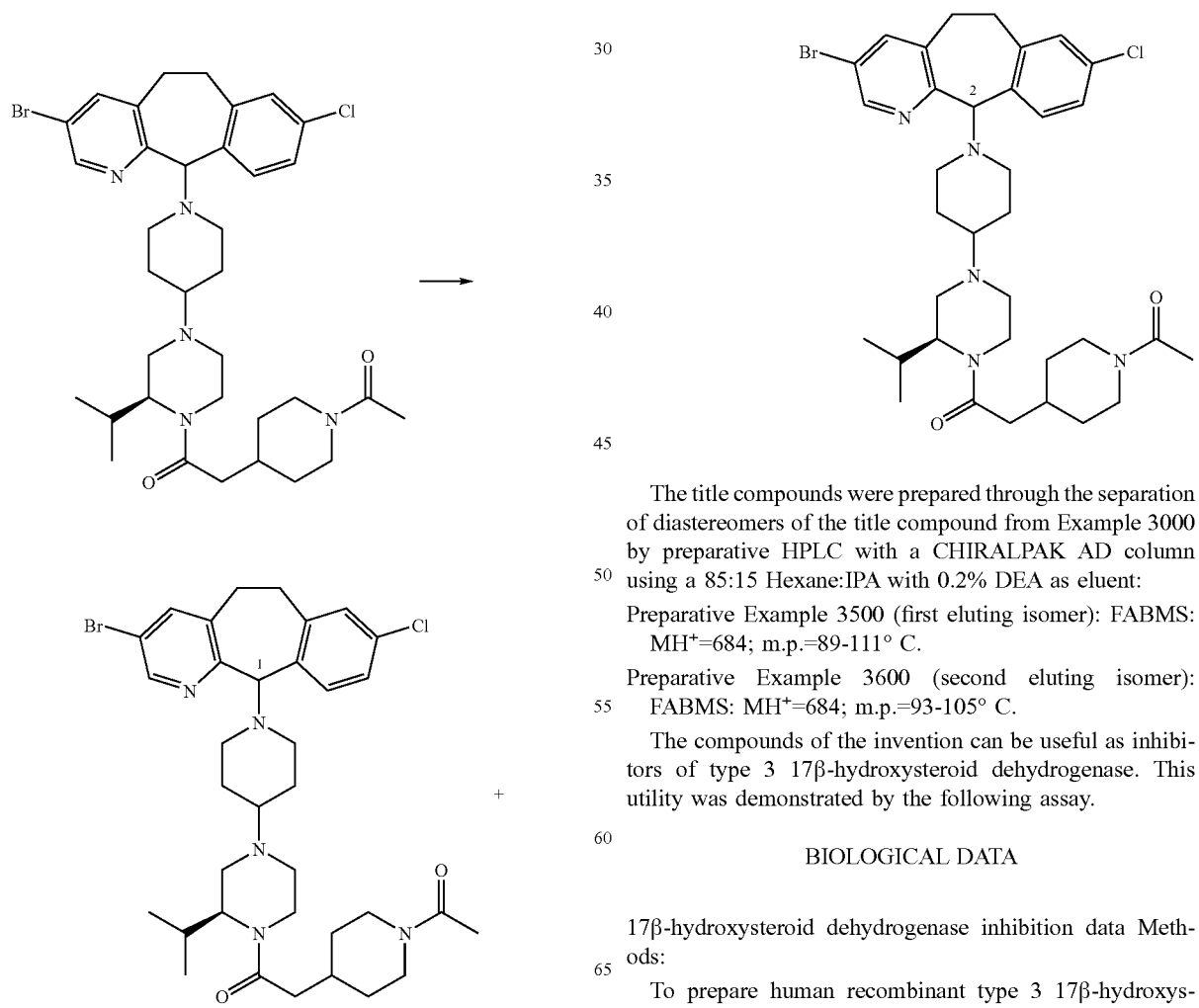

The title compounds were prepared through the separation of diastereomers of the title compound from Example 3000 by preparative HPLC with a CHIRALPAK AD column using a 85:15 Hexane:IPA with 0.2% DEA as eluent:

Preparative Example 3500 (first eluting isomer): FABMS: MH+=684; m.p.=89-111° C.

Preparative Example 3600 (second eluting isomer): FABMS: MH+=684; m.p.=93-105° C.

The compounds of the invention can be useful as inhibitors of type 3 17β-hydroxysteroid dehydrogenase. This utility was demonstrated by the following assay.

BIOLOGICAL DATA

17β-hydroxysteroid dehydrogenase inhibition data Methods:

To prepare human recombinant type 3 17β-hydroxysteroid dehydrogenase enzyme, HEK-293 cells stably transfected with human 17β-HSD type 3 were cultured to confluency and harvested for enzyme. The cells were suspended in isolation buffer (20 mM $KH_2PO_4$, 1 mM EDTA, 0.25 M Sucrose, 1 mM PMSF, 5 □g/ml pepstatin A, 5 µg/ml antipain and 5 □g/ml leupeptin) to a concentration between $5.0 \times 10^6$ and $1.0 \times 10^7$ cells/ml. The cells were sonicated on ice using a micro-ultrasonic cell disrupter at an output setting of No. 40 for four 10 second bursts. The broken cells were then centrifuged at 100,000×g for 60 min at 4° C., and the resulting pellet was resuspended, aliquoted into microfuge tubes, and stored at −80° C.

To measure conversion of $^{14}$C-androstenedione to $^{14}$C-testosterone, reaction buffer (12.5 mM $KH_2PO_4$, 1 mM EDTA), NADPH cofactor (1 mM final), test compound, 17β-HSD3 enzyme (30 µg protein) and $^{14}$C-androstenedione substrate (100 nM; 2.7 nCi/tube) were added to 13×100 borosilicate glass tubes to a total volume of 0.5 mL/tube. The tubes were placed in a prewarmed 37° C. water bath for 30 minutes. The reaction was then stopped by adding 1 ml of ethyl ether. The tubes were centrifuged for 20 minutes at 3000 rpm at 4° C. in a table top centrifuge and then snap frozen in a dry ice-methanol bath. The ether layer was decanted into another glass tube, and then evaporated to dryness using compressed nitrogen gas. The samples were resuspended in chloroform (20 mL) and spotted onto silica G60 thin layer chromatography plates. $^{14}$C-Androstenedione substrate and $^{14}$C-testosterone product were separated by placing the plates in chloroform:ethyl acetate (3:1). The plates were dried, exposed overnight, scanned and quantitated on a FUJI FLA2000 phosphorimager.

Compounds of this invention exhibited a range of 17β-hydroxysteroid dehydrogenase Type 3 binding activity from about 0.025 nM to about >100 nM. Several compounds of this invention have a binding activity in the range of about 0.025 nM to 10 nM.

While the present invention has been described with in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A compound represented by the structural formula:

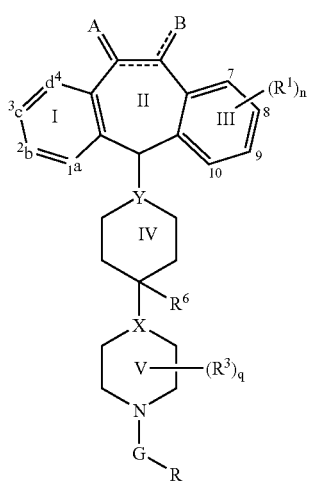

Formula 1 wherein:

X is CH;

Y is N;

G is C(=O);

R is selected from the group consisting of alkyl, —OR$^4$, aryl, heteroaryl, heteroaryloxy, heterocyclyl, heterocyclyloxy, cycloalkyl, cycloalklyloxy, —N(R$^4$)$_2$ where the two R$^4$ moieties can be the same or different, —(CH$_2$)$_n$-aryl, —(CH$_2$)$_n$-heteroaryl, —(CH$_2$)$_n$-heterocyclyl and —(CH$_2$)$_n$-cycloalkyl, wherein each of said alkyl, aryl, heteroaryl, and cycloalkyl can be unsubstituted or optionally independently substituted with one or more moieties which can be the same or different, each moiety being independently selected from the group consisting of alkyl, alkyl, aryl, heteroaryl, —OR$^4$, heterocyclyl, heterocyclyloxy, cycloalkyl, cycloalklyloxy, —N(R$^4$)$_2$ where the two R$^4$ groups can be the same or different, —C(O)R$^4$, and —C(O)N(R$^4$)$_2$ where the two R$^4$ moieties can be the same or different;

one of a, b, c and d in ring I represents N or N$^+$O$^-$, and the remaining a, b, c and d positions represent C(R$^1$) or C(R$^2$); or each of a, b, c, and d are independently selected from C(R$^1$) or C(R$^2$);

R$^1$ and R$^2$ can be the same or different, each being independently selected from the group consisting of:

H, halo, —CF$_3$, —OR$^4$, —C(O)R$^4$, —OCF$^3$, —SR$^4$, —S(O)$_n$R$^5$, benzotriazol-1-yloxy, tetrazol-5-ylthio, alkynyl, alkenyl wherein said alkenyl can be unsubstituted or optionally substituted with halo, —OR$^4$ or —C(O)OR$^4$, alkyl wherein said alkyl can be unsubstituted or optionally substituted with halo, —OR$^4$ or —C(O)OR$^4$, —N(R$^4$)$_2$ where the two R$^4$ moieties can be the same or different, —NO$_2$, —OC(O)R$^5$, —C(O)OR$^4$, —CN, —N(R$^4$)C(O)OR$^4$, —SR$^5$C(O)OR$^4$, and —SR$^5$N(R$^4$)$_2$ (provided that R$^5$ in —SR$^5$N(R$^4$)$_2$ is not —CH$_2$—) wherein each R$^4$ is independently selected;

the dotted line between carbon atoms 5 and 6 represents an optional bond, such that when a double bond is present, A and B can be the same or different, each being independently selected from the group consisting of —R$^4$, halo, —OR$^4$, —C(O)OR$^4$, —OC(O)OR$^4$ or —OC(O)R$^4$, and when no double bond is present between carbon atoms 5 and 6, A and B can be the same or different, each being independently selected from the group consisting of (H$_2$), —(OR$^5$)$_2$, (H and halo), (dihalo), (H and R$^5$), (R$^5$)$_2$, (H and —OC(O)R$^4$), (H and —OR$^4$), (=O), and (H, (=NOR$^4$) or (—O—(CH$_2$)$_p$—O—) wherein p is 2, 3 or 4);

R$^3$ is selected from the group consisting of H, alkyl, alkoxy and alkoxyalkyl;

R$^4$ is selected from the group consisting of H, alkyl, aryl and aralkyl;

R$^5$ is alkyl or aryl;

R$^6$ is H or alkyl;

n is a number from 1-4; and q is a number from 1-8.

2. The compound of claim 1, wherein X is CH.
3. The compound of claim 1, wherein Y is N.
4. The compound of claim 1, wherein R is selected from the group consisting of unsubstituted alkyl, —NH$_2$, and t-butoxy.
5. The compound of claim 1, wherein R is selected from the group consisting of unsubstituted alkyl, alkyl substituted with a heterocyclyl, —NH$_2$, and t-butoxy, wherein said heterocyclyl can be unsubstituted or optionally substituted with one or more moieties selected from the group consisting of —C(O)alkyl, and —C(O)N(alkyl)$_2$ where the two alkyl moieties can be the same or different.
6. A compound of the formula:

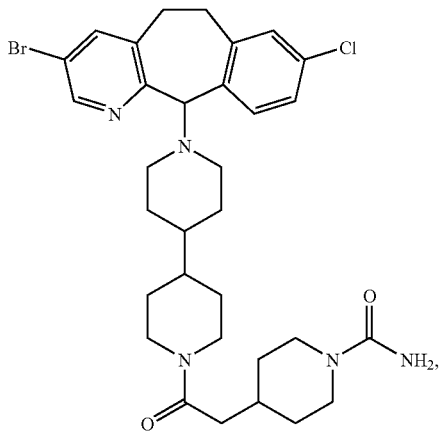

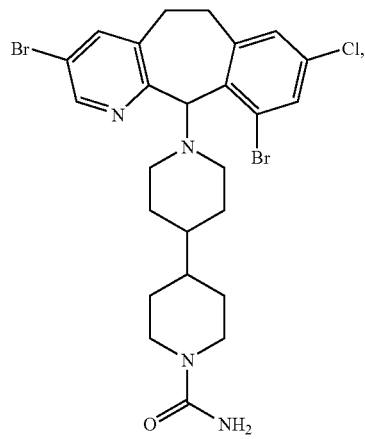

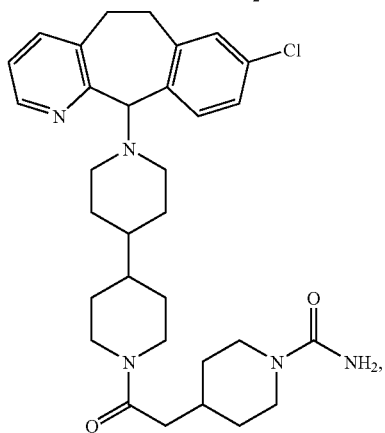

-continued

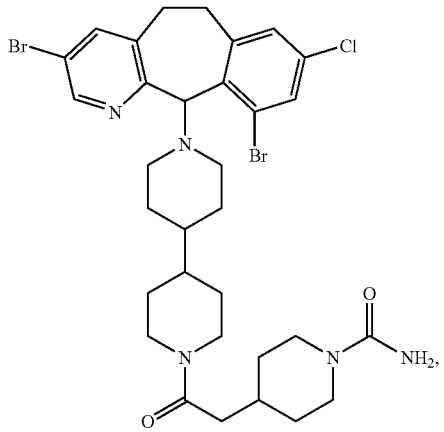

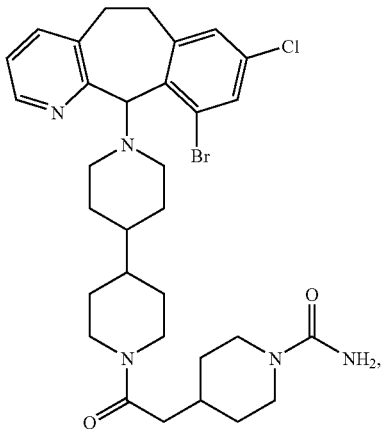

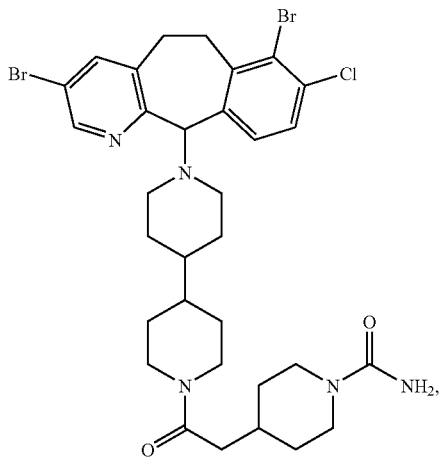

129
-continued
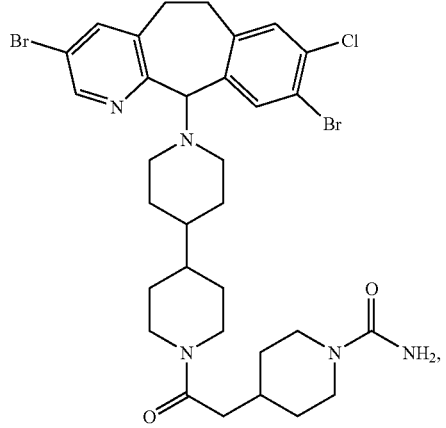
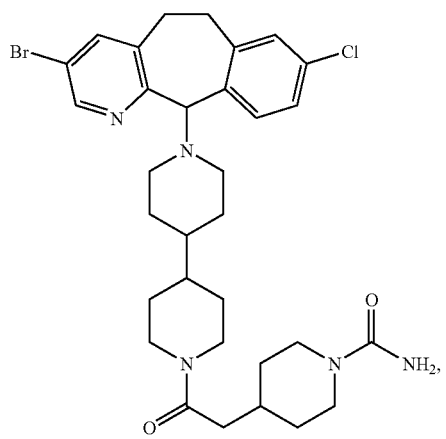
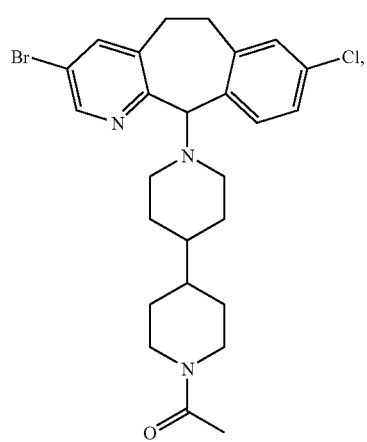
130
-continued
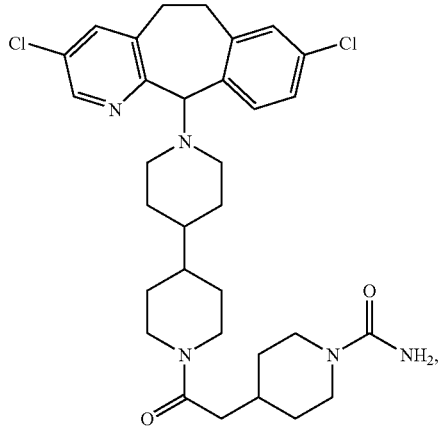
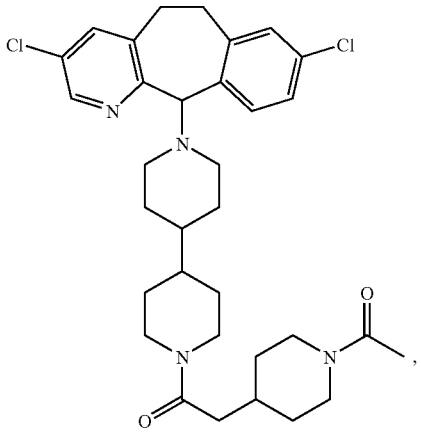
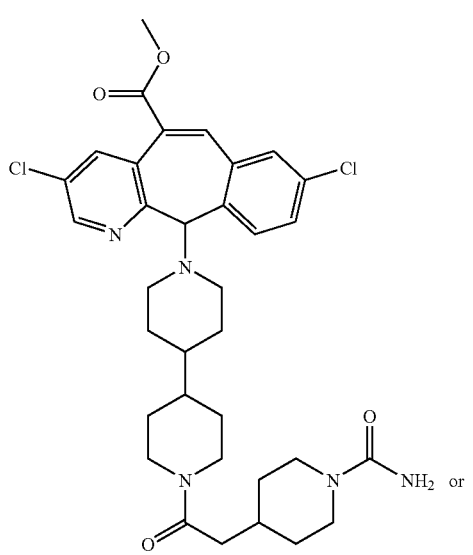

-continued

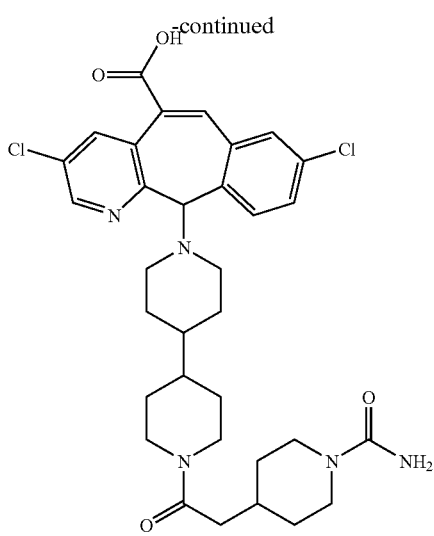

or a pharmaceutically acceptable salt or solvate thereof.

7. A compound of claim 1 in purified form.

8. A pharmaceutical composition comprising a therapeutically effective amount of at least one compound of claim 1 in combination with at least one pharmaceutically acceptable carrier.

9. The pharmaceutical composition of claim 8, additionally comprising one or more agents selected from the group consisting of inhibitors of 5α-reductase type 1, inhibitors of 5α-reductase type 2, flutamide, bicalutamide, LHRH agonists, LHRH antagonists, inhibitors of 17α-hydroxylase/C17-20 lyase, tamsulosin, terazosin, a potassium channel agonist, a 5α-reductase inhibitor, a chemotherapeutic agent and a biological agent optionally in association with at least one method selected from surgery and radiation therapy.

* * * * *